US007615220B2

(12) United States Patent
Huang et al.

(10) Patent No.: US 7,615,220 B2
(45) Date of Patent: Nov. 10, 2009

(54) HIGH AFFINITY HUMAN ANTIBODIES TO HUMAN IL-18 RECEPTOR

(75) Inventors: Tammy H. Huang, Golden Bridge, NY (US); Sean Stevens, Mohegan Lake, NY (US); Joel H. Martin, Putnam Valley, NY (US); Jeanette L. Fairhurst, White Plains, NY (US); Kevin J. Pobursky, Beacon, NY (US); Margaret Karow, Camarillo, CA (US); Joan A. Windsor, Brooklyn, NY (US); Warren R. Mikulka, Brewster, NY (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 320 days.

(21) Appl. No.: 11/784,308

(22) Filed: Apr. 6, 2007

(65) Prior Publication Data

US 2007/0237776 A1    Oct. 11, 2007

Related U.S. Application Data

(60) Provisional application No. 60/790,081, filed on Apr. 7, 2006.

(51) Int. Cl.
*A61K 39/395* (2006.01)
*C07K 16/28* (2006.01)
(52) U.S. Cl. ............. 424/143.1; 424/141.1; 530/388.22
(58) Field of Classification Search ........................ None
See application file for complete search history.

(56) References Cited

U.S. PATENT DOCUMENTS 6,600,022 B1    7/2003   Torigoe et al.
2008/0063644 A1    3/2008   Sekiyama

FOREIGN PATENT DOCUMENTS

WO    WO 2006/009114 A    1/2006

OTHER PUBLICATIONS

Nishida, Y et al. (1998) Cloning and expression of a single-chain Fv fragment . . . Hybridoma 17(6):577-580.
Monoclonal Anti-human IL-18 Ra/IL-1 R5 Antibody (Clone 70625) Feb. 18, 2005 retrieved from the internet : URL:http://www.rndsystems.com/pdf/mab840.p.
Vermot-Desroches, C et al. (2005) Monoclonal antibodies specific for the IL-18 receptor Cellular Immunology 236(1-2):101-104.
Xu, D et al. (1998) Selective expression and functions of interleukin 18 . . . Journal of Experimental Medicine 188(8):1485-1492.
Kitasato, Y et al. (2004) Enhanced expression of interleukin-18 and its receptor in idiopathic . . . American Journal of Respiratory Cell and Molecular Biology 31(6):619-625.

*Primary Examiner*—Prema Mertz
(74) *Attorney, Agent, or Firm*—Valeta Gregg, Esq.

(57) ABSTRACT

An isolated antibody or antibody fragment that binds human interleukin-18 receptor alpha (hIL-18Rα), comprising a light chain variable region (LCVR) selected from the group consisting of SEQ ID NO: 5, 9, 13, 17, 21, 25, 29, 33, 37, 41, 45, 49, 53, 61, 65, 69, 73, 77, and 81 and/or a heavy chain variable region (HCVR) selected from the group consisting of SEQ ID NO: 3, 7, 11, 15, 19, 23, 27, 31, 35, 39, 43, 47, 51, 55, 59, 63, 67, 71, 75, and 79, or a fragment or sequence modified by an amino acid substitution, deletion or addition thereof.

13 Claims, No Drawings

SEQUENCE LISTING

```
<160> NUMBER OF SEQ ID NOS: 91

<210> SEQ ID NO 1
<211> LENGTH: 541
<212> TYPE: PRT
<213> ORGANISM: Artificial Sequence
<220> FEATURE:
<223> OTHER INFORMATION: Synthetic

<400> SEQUENCE: 1

Met Asn Cys Arg Glu Leu Pro Leu Thr Leu Trp Val Leu Ile Ser Val
 1               5                  10                  15

Ser Thr Ala Glu Ser Cys Thr Ser Arg Pro His Ile Thr Val Val Glu
             20                  25                  30

Gly Glu Pro Phe Tyr Leu Lys His Cys Ser Cys Ser Leu Ala His Glu
         35                  40                  45

Ile Glu Thr Thr Thr Lys Ser Trp Tyr Lys Ser Ser Gly Ser Gln Glu
     50                  55                  60

His Val Glu Leu Asn Pro Arg Ser Ser Arg Ile Ala Leu His Asp
 65                  70                  75                  80

Cys Val Leu Glu Phe Trp Pro Val Glu Leu Asn Asp Thr Gly Ser Tyr
                 85                  90                  95

Phe Phe Gln Met Lys Asn Tyr Thr Gln Lys Trp Lys Leu Asn Val Ile
                100                 105                 110

Arg Arg Asn Lys His Ser Cys Phe Thr Glu Arg Gln Val Thr Ser Lys
            115                 120                 125

Ile Val Glu Val Lys Lys Phe Phe Gln Ile Thr Cys Glu Asn Ser Tyr
        130                 135                 140

Tyr Gln Thr Leu Val Asn Ser Thr Ser Leu Tyr Lys Asn Cys Lys Lys
145                 150                 155                 160

Leu Leu Leu Glu Asn Asn Lys Asn Pro Thr Ile Lys Lys Asn Ala Glu
                165                 170                 175

Phe Glu Asp Gln Gly Tyr Tyr Ser Cys Val His Phe Leu His His Asn
            180                 185                 190

Gly Lys Leu Phe Asn Ile Thr Lys Thr Phe Asn Ile Thr Ile Val Glu
        195                 200                 205

Asp Arg Ser Asn Ile Val Pro Val Leu Leu Gly Pro Lys Leu Asn His
    210                 215                 220

Val Ala Val Glu Leu Gly Lys Asn Val Arg Leu Asn Cys Ser Ala Leu
225                 230                 235                 240

Leu Asn Glu Glu Asp Val Ile Tyr Trp Met Phe Gly Glu Glu Asn Gly
                245                 250                 255

Ser Asp Pro Asn Ile His Glu Glu Lys Glu Met Arg Ile Met Thr Pro
```

-continued

```
                     260                 265                 270
Glu Gly Lys Trp His Ala Ser Lys Val Leu Arg Ile Glu Asn Ile Gly
            275                 280                 285
Glu Ser Asn Leu Asn Val Leu Tyr Asn Cys Thr Val Ala Ser Thr Gly
        290                 295                 300
Gly Thr Asp Thr Lys Ser Phe Ile Leu Val Arg Lys Ala Asp Met Ala
305                 310                 315                 320
Asp Ile Pro Gly His Val Phe Thr Arg Gly Met Ile Ile Ala Val Leu
                325                 330                 335
Ile Leu Val Ala Val Cys Leu Val Thr Val Cys Val Ile Tyr Arg
            340                 345                 350
Val Asp Leu Val Leu Phe Tyr Arg His Leu Thr Arg Arg Asp Glu Thr
        355                 360                 365
Leu Thr Asp Gly Lys Thr Tyr Asp Ala Phe Val Ser Tyr Leu Lys Glu
    370                 375                 380
Cys Arg Pro Glu Asn Gly Glu His Thr Phe Ala Val Glu Ile Leu
385                 390                 395                 400
Pro Arg Val Leu Glu Lys His Phe Gly Tyr Lys Leu Cys Ile Phe Glu
                405                 410                 415
Arg Asp Val Val Pro Gly Gly Ala Val Val Asp Glu Ile His Ser Leu
            420                 425                 430
Ile Glu Lys Ser Arg Arg Leu Ile Ile Val Leu Ser Lys Ser Tyr Met
        435                 440                 445
Ser Asn Glu Val Arg Tyr Glu Leu Glu Ser Gly Leu His Glu Ala Leu
    450                 455                 460
Val Glu Arg Lys Ile Lys Ile Ile Leu Ile Glu Phe Thr Pro Val Thr
465                 470                 475                 480
Asp Phe Thr Phe Leu Pro Gln Ser Leu Lys Leu Leu Lys Ser His Arg
                485                 490                 495
Val Leu Lys Trp Lys Ala Asp Lys Ser Leu Ser Tyr Asn Ser Arg Phe
            500                 505                 510
Trp Lys Asn Leu Leu Tyr Leu Met Pro Ala Lys Thr Val Lys Pro Gly
        515                 520                 525
Arg Asp Glu Pro Glu Val Leu Pro Val Leu Ser Glu Ser
    530                 535                 540

<210> SEQ ID NO 2
<211> LENGTH: 363
<212> TYPE: DNA
<213> ORGANISM: Artificial Sequence
<220> FEATURE:
<223> OTHER INFORMATION: Synthetic

<400> SEQUENCE: 2
caggtgcagc tggtgcagtc tggggctgag gtgaagaagc ctggggcctc agtgagggtc       60
tcctgcaagg cttctggata caccttcacc agttatgata tcaactgggt gcgacaggcc     120
actggacagg gcttgaata tgggatgg atgaacccta acagtggtaa cacaggctat        180
gcacagaagt tccagggcag agtctccctg acaagggaca cctccataag cacagcctac    240
atggacctga cagcctgag atctgaggac acggccgtgt attactgtac gaccccaggg     300
gataagtgga actacgaata cttccaattc tggggccagg gcaccctggt caccgtctcc    360
tca                                                                   363

<210> SEQ ID NO 3
```

```
<211> LENGTH: 121
<212> TYPE: PRT
<213> ORGANISM: Artificial Sequence
<220> FEATURE:
<223> OTHER INFORMATION: Synthetic

<400> SEQUENCE: 3

Gln Val Gln Leu Val Gln Ser Gly Ala Glu Val Lys Lys Pro Gly Ala
1               5                   10                  15

Ser Val Arg Val Ser Cys Lys Ala Ser Gly Tyr Thr Phe Thr Ser Tyr
            20                  25                  30

Asp Ile Asn Trp Val Arg Gln Ala Thr Gly Gln Gly Leu Glu Tyr Met
        35                  40                  45

Gly Trp Met Asn Pro Asn Ser Gly Asn Thr Gly Tyr Ala Gln Lys Phe
    50                  55                  60

Gln Gly Arg Val Ser Leu Thr Arg Asp Thr Ser Ile Ser Thr Ala Tyr
65                  70                  75                  80

Met Asp Leu Asn Ser Leu Arg Ser Glu Asp Thr Ala Val Tyr Tyr Cys
                85                  90                  95

Thr Thr Pro Gly Asp Lys Trp Asn Tyr Glu Tyr Phe Gln Phe Trp Gly
            100                 105                 110

Gln Gly Thr Leu Val Thr Val Ser Ser
        115                 120

<210> SEQ ID NO 4
<211> LENGTH: 318
<212> TYPE: DNA
<213> ORGANISM: Artificial Sequence
<220> FEATURE:
<223> OTHER INFORMATION: Synthetic

<400> SEQUENCE: 4
gacatccaga tgacccagtc tccatcttcc gtgtctgcat ctgtcggaga cagagtcacc      60
atcacttgtc gggcgagtca acatattagc atctggttag cctggtatca gcagaaacca    120
gggaaagccc ctaaactcct gatcttgtct gcatccagtt tgctaagtgg ggtcccatca    180
aggttcagcg gcagtggatc tgggacagat ttcgccctca ccgtcagcag cctgcagcct    240
gaagattttg caacttacta ttgtcaacag gcaaacagtt tccccagttt cggccctggg    300
accaaagtgg aaatcaaa                                                   318

<210> SEQ ID NO 5
<211> LENGTH: 106
<212> TYPE: PRT
<213> ORGANISM: Artificial Sequence
<220> FEATURE:
<223> OTHER INFORMATION: Synthetic

<400> SEQUENCE: 5

Asp Ile Gln Met Thr Gln Ser Pro Ser Ser Val Ser Ala Ser Val Gly
1               5                   10                  15

Asp Arg Val Thr Ile Thr Cys Arg Ala Ser Gln His Ile Ser Ile Trp
            20                  25                  30

Leu Ala Trp Tyr Gln Gln Lys Pro Gly Lys Ala Pro Lys Leu Leu Ile
        35                  40                  45

Leu Ser Ala Ser Ser Leu Leu Ser Gly Val Pro Ser Arg Phe Ser Gly
    50                  55                  60

Ser Gly Ser Gly Thr Asp Phe Ala Leu Thr Val Ser Ser Leu Gln Pro
65                  70                  75                  80
```

Glu Asp Phe Ala Thr Tyr Tyr Cys Gln Gln Ala Asn Ser Phe Pro Ser
                85                  90                  95

Phe Gly Pro Gly Thr Lys Val Glu Ile Lys
            100                 105

<210> SEQ ID NO 6
<211> LENGTH: 384
<212> TYPE: DNA
<213> ORGANISM: Artificial Sequence
<220> FEATURE:
<223> OTHER INFORMATION: Synthetic

<400> SEQUENCE: 6
caggttcagc tggtgcagtc tggagctgag gtgaagaagc ctggggcctc agtgaaggtc      60
tcctgcaagg cttctggtta cacctttaat agttatggaa tcagctgggt gcgacaggcc    120
cctggacaag ggcttgagtg gatgggatgg atcagaactt acaatggtaa cacaaactat    180
gcacagaagc tccagggcag agtcaccatg accacagaca tccacgag cacagcctac      240 atggagctga ggagcctgag atctgacgac acggccgtgt attactgtgc gagagatgag    300
gcccgtatag tagtggctgg tacaactcct tactactacg gtatggacgt ctggggccaa    360
gggaccacgg tcaccgtctc ctca                                           384

<210> SEQ ID NO 7
<211> LENGTH: 128
<212> TYPE: PRT
<213> ORGANISM: Artificial Sequence
<220> FEATURE:
<223> OTHER INFORMATION: Synthetic

<400> SEQUENCE: 7

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Asn Ser Tyr
            20                  25                  30

Gly Ile Ser Trp Val Arg Gln Ala Pro Gly Gln Gly Leu Glu Trp Met
        35                  40                  45

Gly Trp Ile Arg Thr Tyr Asn Gly Asn Thr Asn Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Asp Glu Ala Arg Ile Val Val Ala Gly Thr Thr Pro Tyr Tyr
            100                 105                 110

Tyr Gly Met Asp Val Trp Gly Gln Gly Thr Thr Val Thr Val Ser Ser
        115                 120                 125

<210> SEQ ID NO 8
<211> LENGTH: 321
<212> TYPE: DNA
<213> ORGANISM: Artificial Sequence
<220> FEATURE:
<223> OTHER INFORMATION: Synthetic

<400> SEQUENCE: 8
gccatccaga tgacccagtc tccatcctcc ctgtctgcat ctgtaggaga cagagtcacc      60
atcacttgcc gggcaagtca ggacattaga aatgatttag ctggtttca gcagaaacca     120 gggaaagccc ctaagctcct gatctatgct gcatccagtt tacaaagtgg ggtcccatca    180

```
aggttcagcg gcagtggatc tggcacagat tcactctca ccatcagcag cctgcagcct    240
gaagattttg caacttatta ctgtctacaa gattacaatt accctcggac gttcggccaa    300
gggaccaagg tggaaatcaa a                                              321
```

<210> SEQ ID NO 9
<211> LENGTH: 107
<212> TYPE: PRT
<213> ORGANISM: Artificial Sequence
<220> FEATURE:
<223> OTHER INFORMATION: Synthetic

<400> SEQUENCE: 9

```
Ala Ile Gln Met Thr Gln Ser Pro Ser Ser Leu Ser Ala Ser Val Gly
 1               5                  10                  15

Asp Arg Val Thr Ile Thr Cys Arg Ala Ser Gln Asp Ile Arg Asn Asp
            20                  25                  30

Leu Gly Trp Phe Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Leu Gln Asp Tyr Asn Tyr Pro Arg
                85                  90                  95

Thr Phe Gly Gln Gly Thr Lys Val Glu Ile Lys
            100                 105
```

<210> SEQ ID NO 10
<211> LENGTH: 345
<212> TYPE: DNA
<213> ORGANISM: Artificial Sequence
<220> FEATURE:
<223> OTHER INFORMATION: Synthetic

<400> SEQUENCE: 10

```
caggttcagc tggtgcagtc tggagctgag gtgaagaagc ctggggcctc aatgaaggtc     60
tcctgcaagg cttctggtta cacctttacc aactttggta tcagctgggt gcgacaggcc    120
cctggacaag gcttgagtg gatgggatgg atcagcgctt acaatggtaa cacaaactat    180
gcacagaagc tccagggcag agtcaccatg accacagaca catccacgag cacagcctac    240
atggagctga ggagcctgag atctgacgac acggccgtgt attactgtgc gagagggtgg    300
ttcttcgata tctggggccg tggcaccctg gtcactgtct cctca                    345
```

<210> SEQ ID NO 11
<211> LENGTH: 115
<212> TYPE: PRT
<213> ORGANISM: Artificial Sequence
<220> FEATURE:
<223> OTHER INFORMATION: Synthetic

<400> SEQUENCE: 11

```
Gln Val Gln Leu Val Gln Ser Gly Ala Glu Val Lys Lys Pro Gly Ala
 1               5                  10                  15

Ser Met Lys Val Ser Cys Lys Ala Ser Gly Tyr Thr Phe Thr Asn Phe
            20                  25                  30

Gly Ile Ser Trp Val Arg Gln Ala Pro Gly Gln Gly Leu Glu Trp Met
        35                  40                  45
```

```
Gly Trp Ile Ser Ala Tyr Asn Gly Asn Thr Asn Tyr Ala Gln Lys Leu
 50                  55                  60

Gln Gly Arg Val Thr Met Thr Thr Asp Thr Ser Thr Ser Thr Ala Tyr
 65                  70                  75                  80

Met Glu Leu Arg Ser Leu Arg Ser Asp Asp Thr Ala Val Tyr Tyr Cys
                 85                  90                  95

Ala Arg Gly Trp Phe Phe Asp Ile Trp Gly Arg Gly Thr Leu Val Thr
                100                 105                 110

Val Ser Ser
        115

<210> SEQ ID NO 12
<211> LENGTH: 339
<212> TYPE: DNA
<213> ORGANISM: Artificial Sequence
<220> FEATURE:
<223> OTHER INFORMATION: Synthetic

<400> SEQUENCE: 12
gacatcgtga tgacccagtc tccagactcc ctggctgtgt ctctgggcga gagggccacc     60
atcaactgca agtccagcca gagtgtttta tacagctcca acaataagaa ctatttagct    120
tggtaccagc agaaaccagg acagcctcct aagttgctca tttactgggc atctacccgg    180
gaatccgggg tccctgaccg attcagtggc agcgggtctg ggacagattt cactctcacc    240
atcagcagcc tgcaggctga agatgtggca gtttattatt gtcagcaata ttatagaact    300
ccgtacactt ttggccaggg gaccaagctg gagatcaaa                           339

<210> SEQ ID NO 13
<211> LENGTH: 113
<212> TYPE: PRT
<213> ORGANISM: Artificial Sequence
<220> FEATURE:
<223> OTHER INFORMATION: Synthetic

<400> SEQUENCE: 13

Asp Ile Val Met Thr Gln Ser Pro Asp Ser Leu Ala Val Ser Leu Gly
  1               5                  10                  15

Glu Arg Ala Thr Ile Asn Cys Lys Ser Ser Gln Ser Val Leu Tyr Ser
                 20                  25                  30

Ser Asn Asn Lys Asn Tyr Leu Ala Trp Tyr Gln Gln Lys Pro Gly Gln
             35                  40                  45

Pro Pro Lys Leu Leu Ile Tyr Trp Ala Ser Thr Arg Glu Ser Gly Val
     50                  55                  60

Pro Asp Arg Phe Ser Gly Ser Gly Ser Gly Thr Asp Phe Thr Leu Thr
 65                  70                  75                  80

Ile Ser Ser Leu Gln Ala Glu Asp Val Ala Val Tyr Tyr Cys Gln Gln
                 85                  90                  95

Tyr Tyr Arg Thr Pro Tyr Thr Phe Gly Gln Gly Thr Lys Leu Glu Ile
                100                 105                 110

Lys

<210> SEQ ID NO 14
<211> LENGTH: 345
<212> TYPE: DNA
<213> ORGANISM: Artificial Sequence
<220> FEATURE:
<223> OTHER INFORMATION: Synthetic

<400> SEQUENCE: 14
```

```
caggttcagc tggtgcagtc tggagctgag gtgaagaagc ctggggcctc agtgaaggtc      60
tcctgcaagg cttctggtta caactttatc agctatggta tcagctgggt gcgacaggcc     120
cctggacaag gcttgagtg gatgggatgg atcaccactt acaatggtaa cacaaactat      180
gcacagaagc tccagggcag agtcaccatg accacagaca catccacgag cacagcctac     240
atggagctga ggagcctgag atctgacgac acggccgtgt attactgtgc gagagggtgg     300
tacttcgatc tctggggccg tggcaccctg gtcactgtct cctca                    345
```

<210> SEQ ID NO 15
<211> LENGTH: 115
<212> TYPE: PRT
<213> ORGANISM: Artificial Sequence
<220> FEATURE:
<223> OTHER INFORMATION: Synthetic

<400> SEQUENCE: 15

```
Gln Val Gln Leu Val Gln Ser Gly Ala Glu Val Lys Lys Pro Gly Ala
  1               5                  10                  15

Ser Val Lys Val Ser Cys Lys Ala Ser Gly Tyr Asn Phe Ile Ser Tyr
             20                  25                  30

Gly Ile Ser Trp Val Arg Gln Ala Pro Gly Gln Gly Leu Glu Trp Met
         35                  40                  45

Gly Trp Ile Thr Thr Tyr Asn Gly Asn Thr Asn Tyr Ala Gln Lys Leu
     50                  55                  60

Gln Gly Arg Val Thr Met Thr Thr Asp Thr Ser Thr Ser Thr Ala Tyr
 65                  70                  75                  80

Met Glu Leu Arg Ser Leu Arg Ser Asp Asp Thr Ala Val Tyr Tyr Cys
                 85                  90                  95

Ala Arg Gly Trp Tyr Phe Asp Leu Trp Gly Arg Gly Thr Leu Val Thr
            100                 105                 110

Val Ser Ser
        115
```

<210> SEQ ID NO 16
<211> LENGTH: 339
<212> TYPE: DNA
<213> ORGANISM: Artificial Sequence
<220> FEATURE:
<223> OTHER INFORMATION: Synthetic

<400> SEQUENCE: 16

```
gacatcgtga tgacccagtc tccagactcc ctggctgtgt ctctgggcga gagggccacc      60
atcaactgca gtccagtca gagtgttttt tacagctcca acaataagaa ctacttagct     120
tggtaccagc agaaacctgg acagcctcct aacctgctca tttactgggc atctacccgg     180
gaatccgggg tccctgaccg attcagtggc agcgggtctg gacagattt cactctcacc     240 atcagcagcc tgcaggctga agatgtggca gtttattact gtcagcaata ttatcgtact     300
ccgtacactt ttggccaagg gaccaagctg gagatcaaa                            339
```

<210> SEQ ID NO 17
<211> LENGTH: 113
<212> TYPE: PRT
<213> ORGANISM: Artificial Sequence
<220> FEATURE:
<223> OTHER INFORMATION: Synthetic

<400> SEQUENCE: 17

Asp Ile Val Met Thr Gln Ser Pro Asp Ser Leu Ala Val Ser Leu Gly
1               5                   10                  15

Glu Arg Ala Thr Ile Asn Cys Lys Ser Gln Ser Val Phe Tyr Ser
            20                  25                  30

Ser Asn Asn Lys Asn Tyr Leu Ala Trp Tyr Gln Lys Pro Gly Gln
        35                  40                  45

Pro Pro Asn Leu Leu Ile Tyr Trp Ala Ser Thr Arg Glu Ser Gly Val
50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Arg Thr Pro Tyr Thr Phe Gly Gln Gly Thr Lys Leu Glu Ile
            100                 105                 110

Lys

<210> SEQ ID NO 18
<211> LENGTH: 345
<212> TYPE: DNA
<213> ORGANISM: Artificial Sequence
<220> FEATURE:
<223> OTHER INFORMATION: Synthetic

<400> SEQUENCE: 18
caggttcagc tggtgcagtc tggaactgag gtgaggaagc ctggggcctc agtgaaggtc      60
tcctgcaagg cctctggtta caccttacc agctatggta tcagctgggt gcgacaggcc     120
cctggtcaag gcttgagtg gatgggatgg atcagcgctt ataatggaaa cacagactat     180
gcactgaagc tccaggacag agtcaccatg accacagaca catccacgaa cacagcctac     240
atggagctga ggagcctgag atctgacgac acggccgtgt attactgtgc gaggggctgg     300
tacttcgctc tctggggccg tggcaccctg gtcactgtct cctca                    345

<210> SEQ ID NO 19
<211> LENGTH: 115
<212> TYPE: PRT
<213> ORGANISM: Artificial Sequence
<220> FEATURE:
<223> OTHER INFORMATION: Synthetic

<400> SEQUENCE: 19

Gln Val Gln Leu Val Gln Ser Gly Thr Glu Val Arg Lys Pro Gly Ala
1               5                   10                  15

Ser Val Lys Val Ser Cys Lys Ala Ser Gly Tyr Thr Phe Thr Ser Tyr
            20                  25                  30

Gly Ile Ser Trp Val Arg Gln Ala Pro Gly Gln Gly Leu Glu Trp Met
        35                  40                  45

Gly Trp Ile Ser Ala Tyr Asn Gly Asn Thr Asp Tyr Ala Leu Lys Leu
    50                  55                  60

Gln Asp Arg Val Thr Met Thr Thr Asp Thr Ser Thr Asn Thr Ala Tyr
65                  70                  75                  80

Met Glu Leu Arg Ser Leu Arg Ser Asp Asp Thr Ala Val Tyr Tyr Cys
                85                  90                  95

Ala Arg Gly Trp Tyr Phe Ala Leu Trp Gly Arg Gly Thr Leu Val Thr
            100                 105                 110

Val Ser Ser
        115

<210> SEQ ID NO 20
<211> LENGTH: 339
<212> TYPE: DNA
<213> ORGANISM: Artificial Sequence
<220> FEATURE:
<223> OTHER INFORMATION: Synthetic

<400> SEQUENCE: 20

```
gacatcgtgc tgacccagtc tccagactcc ctggctgtgt ctctgggcga gagggccacc      60
atcaactgca ggtccagcca gagtgtttta tacagctcca acaataggaa ctacttagct     120
tggtaccagc ataaaccagg acagcctcct aagttgctca tttactgggc atctacccgg     180
gagtccgggg tccctgaccg attcagtggc agcgggtctg ggactgattt cactctcacc     240
atcagcagtc tgcaggctga agatgtggca gtttattact gtcagcaatt ttatcgtact     300
ccgtacactt ttggccaggg gaccaagctg gagatcaaa                            339
```

<210> SEQ ID NO 21
<211> LENGTH: 113
<212> TYPE: PRT
<213> ORGANISM: Artificial Sequence
<220> FEATURE:
<223> OTHER INFORMATION: Synthetic

<400> SEQUENCE: 21

```
Asp Ile Val Leu Thr Gln Ser Pro Asp Ser Leu Ala Val Ser Leu Gly
 1               5                  10                  15

Glu Arg Ala Thr Ile Asn Cys Arg Ser Ser Gln Ser Val Leu Tyr Ser
            20                  25                  30

Ser Asn Asn Arg Asn Tyr Leu Ala Trp Tyr Gln His Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Phe Tyr Arg Thr Pro Tyr Thr Phe Gly Gln Gly Thr Lys Leu Glu Ile
            100                 105                 110

Lys
```

<210> SEQ ID NO 22
<211> LENGTH: 345
<212> TYPE: DNA
<213> ORGANISM: Artificial Sequence
<220> FEATURE:
<223> OTHER INFORMATION: Synthetic

<400> SEQUENCE: 22

```
caggttcagc tggtgcagtc tggagctgag gtgaagaagc ctggggcctc agtgaaggtc      60
tcctgcaagg cttctggtta cacctttacc agctatggta tcagctgggt gcgacaggcc     120
cctggacaag ggcttgagtg gatgggatgg atcagcgttt acaatggtaa cacaaactat     180
gcacagaagc accagggcag agtcaccatg accacagaca catccacgag cacagcctac     240
atggagctga ggagcctgag atctgacgac acggccgtat attactgtgc gagagggtgg     300
tacttcgatc tctggggccg tggcaccctg gtcactgtct cctca                     345
```

<210> SEQ ID NO 23

-continued

```
<211> LENGTH: 115
<212> TYPE: PRT
<213> ORGANISM: Artificial Sequence
<220> FEATURE:
<223> OTHER INFORMATION: Synthetic

<400> SEQUENCE: 23
```

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Gly Ile Ser Trp Val Arg Gln Ala Pro Gly Gln Gly Leu Glu Trp Met
        35                  40                  45

Gly Trp Ile Ser Val Tyr Asn Gly Asn Thr Asn Tyr Ala Gln Lys His
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Gly Trp Tyr Phe Asp Leu Trp Gly Arg Gly Thr Leu Val Thr
            100                 105                 110

Val Ser Ser
        115

```
<210> SEQ ID NO 24
<211> LENGTH: 339
<212> TYPE: DNA
<213> ORGANISM: Artificial Sequence
<220> FEATURE:
<223> OTHER INFORMATION: Synthetic

<400> SEQUENCE: 24
```
gacatcgtga tgacccagtc tccagactcc ctggctgtgt ctctgggcga gagggccacc      60
atcaactgca agtccagcca gactgtttta tacagctcca acaataagac ctacttagct     120
tggtaccagc agaaaccagg acagcctcct aagctgctca tttactgggc atctacccgg     180
gaatccgggg tccctgaccg attcagtggc agcgggtctg ggacagattt cactctcacc     240
atcagcagcc tgcaggctga agatgtggca gtttattact gtcagcaata ttatcgtact     300
ccgtacactt ttggccaggg gaccaagctg gagatcaaa                            339

```
<210> SEQ ID NO 25
<211> LENGTH: 113
<212> TYPE: PRT
<213> ORGANISM: Artificial Sequence
<220> FEATURE:
<223> OTHER INFORMATION: Synthetic

<400> SEQUENCE: 25
```

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Thr Val Leu Tyr Ser
            20                  25                  30

Ser Asn Asn Lys Thr Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

```
Ile Ser Ser Leu Gln Ala Glu Asp Val Ala Val Tyr Tyr Cys Gln Gln
                85                  90                  95

Tyr Tyr Arg Thr Pro Tyr Thr Phe Gly Gln Gly Thr Lys Leu Glu Ile
            100                 105                 110

Lys

<210> SEQ ID NO 26
<211> LENGTH: 345
<212> TYPE: DNA
<213> ORGANISM: Artificial Sequence
<220> FEATURE:
<223> OTHER INFORMATION: Synthetic

<400> SEQUENCE: 26
caggttcagc tggtgcagtc tggagctgag gtgaagaagc ctggggcctc agtgaaggtc      60
tcctgcaagg cttctggtta cacctttagc agctatggta tcagctgggt gcgacaggcc     120
cctggacaag gacttgagtg gatgggctgg atcagcgttt acaatggtaa cacagactat     180
gcacagaagt tccagggcag agtcaccatg accacagaca catccacgag cacagcctac     240
atggagctga ggagcctgag atctgacgac acggccatat atttctgtac gagagggtgg     300
tatttcgatc tctggggccg tggcaccctg gtcactgtct cctca                    345

<210> SEQ ID NO 27
<211> LENGTH: 115
<212> TYPE: PRT
<213> ORGANISM: Artificial Sequence
<220> FEATURE:
<223> OTHER INFORMATION: Synthetic

<400> SEQUENCE: 27

Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Ser Ser Tyr
            20                  25                  30

Gly Ile Ser Trp Val Arg Gln Ala Pro Gly Gln Gly Leu Glu Trp Met
        35                  40                  45

Gly Trp Ile Ser Val Tyr Asn Gly Asn Thr Asp Tyr Ala Gln Lys Phe
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Ile Tyr Phe Cys
                85                  90                  95

Thr Arg Gly Trp Tyr Phe Asp Leu Trp Gly Arg Gly Thr Leu Val Thr
            100                 105                 110

Val Ser Ser
        115

<210> SEQ ID NO 28
<211> LENGTH: 339
<212> TYPE: DNA
<213> ORGANISM: Artificial Sequence
<220> FEATURE:
<223> OTHER INFORMATION: Synthetic

<400> SEQUENCE: 28
gacatcgtga tgacccagtc tccagactcc ctggctgtgt ctctgggcga gagggccacc      60
atcaactgca gtccagcca gactgtttta tacagctcca acaataagaa ctacttagct      120
tggtaccagc agaaaccagg acagcctcct accctgctca tttactggtc atctacccgg     180
```

```
gaatccgggg tccctgaccg attcagtggc ggcgggtctg ggacagattt cactctcacc      240
atcagcagcc tgcaggctga agatgtggca atttattact gtcagcaata ttatcgtact      300
ccgtacactt ttggccaggg gaccaagctg gacatcaaa                             339
```

<210> SEQ ID NO 29
<211> LENGTH: 113
<212> TYPE: PRT
<213> ORGANISM: Artificial Sequence
<220> FEATURE:
<223> OTHER INFORMATION: Synthetic

<400> SEQUENCE: 29

```
Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Thr Val Leu Tyr Ser
            20                  25                  30

Ser Asn Asn Lys Asn Tyr Leu Ala Trp Tyr Gln Lys Pro Gly Gln
        35                  40                  45

Pro Pro Thr Leu Leu Ile Tyr Trp Ser Ser Thr Arg Glu Ser Gly Val
    50                  55                  60

Pro Asp Arg Phe Ser Gly Gly Ser Gly Thr Asp Phe Thr Leu Thr
65                  70                  75                  80

Ile Ser Ser Leu Gln Ala Glu Asp Val Ala Ile Tyr Tyr Cys Gln Gln
                85                  90                  95

Tyr Tyr Arg Thr Pro Tyr Thr Phe Gly Gln Gly Thr Lys Leu Asp Ile
            100                 105                 110

Lys
```

<210> SEQ ID NO 30
<211> LENGTH: 354
<212> TYPE: DNA
<213> ORGANISM: Artificial Sequence
<220> FEATURE:
<223> OTHER INFORMATION: Synthetic

<400> SEQUENCE: 30

```
caggtgcaac tggtgcagtc tggggctgag gtgaagaagc ctggggcctc agtgaaggtc      60
tcctgcaagg cttctggata caccttcacc ggctactata tgcactgggt gcgacaggcc      120
cctggacaag gcttgagtg gatgggatgg atcaaccta acagtggtgg cacaaactat        180
gcacagaagt tcagggcag ggtcaccatg accaggaca cgtccatcag cacagcctac        240
atggagctga gcagactgag atctgacgac acggccgtgt attactgtgc gcgagatatg      300
ggggacctat ttttgactac tggggccag ggaaccctgg tcaccgtctc ctca             354
```

<210> SEQ ID NO 31
<211> LENGTH: 118
<212> TYPE: PRT
<213> ORGANISM: Artificial Sequence
<220> FEATURE:
<223> OTHER INFORMATION: Synthetic

<400> SEQUENCE: 31

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
```

```
              35                  40                  45
Gly Trp Ile Asn Pro Asn Ser Gly Gly Thr Asn Tyr Ala Gln Lys Phe
         50                  55                  60

Gln Gly Arg Val Thr Met Thr Arg Asp Thr Ser Ile Ser Thr Ala Tyr
 65                  70                  75                  80

Met Glu Leu Ser Arg Leu Arg Ser Asp Thr Ala Val Tyr Tyr Cys
                 85                  90                  95

Ala Arg Asp Met Gly Asp Leu Phe Phe Asp Tyr Trp Gly Gln Gly Thr
             100                 105                 110

Leu Val Thr Val Ser Ser
            115

<210> SEQ ID NO 32
<211> LENGTH: 336
<212> TYPE: DNA
<213> ORGANISM: Artificial Sequence
<220> FEATURE:
<223> OTHER INFORMATION: Synthetic

<400> SEQUENCE: 32
gacatcgtga tgacccagtc tccagactcc ctggctgtgt ctctgggcga gagggccacc      60
atcaactgca gtccagcca gagtgttttt tacagctcca acaataagaa ctacttggct     120
tggttccagc agaaaccagg acagcctcct aaactgctca tttactgggc atctacccgg     180
gaatccgggg tccctgaccg attcagtggc agcgggtctg ggacagattt cactctcacc     240
atcagcagcc tgcaggctga agatgtggca gtttattact gtcaacaata ttttattact     300
tggacgttcg gccaagggac caaggtggaa atcaaa                               336

<210> SEQ ID NO 33
<211> LENGTH: 112
<212> TYPE: PRT
<213> ORGANISM: Artificial Sequence
<220> FEATURE:
<223> OTHER INFORMATION: Synthetic

<400> SEQUENCE: 33

Asp Ile Val Met Thr Gln Ser Pro Asp Ser Leu Ala Val Ser Leu Gly
 1               5                  10                  15

Glu Arg Ala Thr Ile Asn Cys Lys Ser Ser Gln Ser Val Phe Tyr Ser
             20                  25                  30

Ser Asn Asn Lys Asn Tyr Leu Ala Trp Phe Gln Gln Lys Pro Gly Gln
         35                  40                  45

Pro Pro Lys Leu Leu Ile Tyr Trp Ala Ser Thr Arg Glu Ser Gly Val
     50                  55                  60

Pro Asp Arg Phe Ser Gly Ser Gly Ser Gly Thr Asp Phe Thr Leu Thr
 65                  70                  75                  80

Ile Ser Ser Leu Gln Ala Glu Asp Val Ala Val Tyr Tyr Cys Gln Gln
                 85                  90                  95

Tyr Phe Ile Thr Trp Thr Phe Gly Gln Gly Thr Lys Val Glu Ile Lys
            100                 105                 110

<210> SEQ ID NO 34
<211> LENGTH: 357
<212> TYPE: DNA
<213> ORGANISM: Artificial Sequence
<220> FEATURE:
<223> OTHER INFORMATION: Synthetic

<400> SEQUENCE: 34
```

```
caggtgcagc tgcaggagtc aggtccagga ctggtgcaga cctcgcagac cctctcactc    60
acctgtgcca tctccgggga cagtgtctct acctacagtg ctgcttggaa ctggatcagg   120
cagtccccat cgagaggcct gagtggctg  ggaagaacat actacaggtc cgagtggtat   180
aatcattatg cagtatctct gaaaggtcga ttaaccatca acccagacac atccaagaac   240
cagttctccc tgcaactgaa ctctgtgaat cccgaggaca cggctattta ttactgtgtg   300
agagagggag atgcttttga tatctggggc caaggggcaa tggtcaccgt ctcttca      357
```

```
<210> SEQ ID NO 35
<211> LENGTH: 119
<212> TYPE: PRT
<213> ORGANISM: Artificial Sequence
<220> FEATURE:
<223> OTHER INFORMATION: Synthetic

<400> SEQUENCE: 35
```

Gln Val Gln Leu Gln Glu Ser Gly Pro Gly Leu Val Gln Thr Ser Gln
 1               5                  10                  15

Thr Leu Ser Leu Thr Cys Ala Ile Ser Gly Asp Ser Val Ser Thr Tyr
            20                  25                  30

Ser Ala Ala Trp Asn Trp Ile Arg Gln Ser Pro Ser Arg Gly Leu Glu
        35                  40                  45

Trp Leu Gly Arg Thr Tyr Tyr Arg Ser Glu Trp Tyr Asn His Tyr Ala
    50                  55                  60

Val Ser Leu Lys Gly Arg Leu Thr Ile Asn Pro Asp Thr Ser Lys Asn
65                  70                  75                  80

Gln Phe Ser Leu Gln Leu Asn Ser Val Asn Pro Glu Asp Thr Ala Ile
                85                  90                  95

Tyr Tyr Cys Val Arg Glu Gly Asp Ala Phe Asp Ile Trp Gly Gln Gly
            100                 105                 110

Ala Met Val Thr Val Ser Ser
            115

```
<210> SEQ ID NO 36
<211> LENGTH: 321
<212> TYPE: DNA
<213> ORGANISM: Artificial Sequence
<220> FEATURE:
<223> OTHER INFORMATION: Synthetic

<400> SEQUENCE: 36
gaaattgtgt tgacacagtc tccagccacc ctgtctttgt ctccagggga aagagccacc    60
ctctcctgca gggccagtca gagtgttagc agctacttag cctggtaccg acagagacct   120
ggccaggctc ccaggctcct catctatgat gcgtctaata gggccactgg catcccagcc   180
aggttcagtg gcagtgggtc tgggacagac ttcactctca ccatcagcag cctagagcct   240
gaagattttg cagtttatta ctgtcagcag cgtggcaatt ggcctcctac tttcggcgga   300
gggaccaagg tggagatcaa a                                             321
```

```
<210> SEQ ID NO 37
<211> LENGTH: 107
<212> TYPE: PRT
<213> ORGANISM: Artificial Sequence
<220> FEATURE:
<223> OTHER INFORMATION: Synthetic

<400> SEQUENCE: 37
```

```
Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Arg Gln Arg Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65              70                  75                  80

Glu Asp Phe Ala Val Tyr Tyr Cys Gln Gln Arg Gly Asn Trp Pro Pro
                85                  90                  95

Thr Phe Gly Gly Gly Thr Lys Val Glu Ile Lys
            100                 105
```

```
<210> SEQ ID NO 38
<211> LENGTH: 345
<212> TYPE: DNA
<213> ORGANISM: Artificial Sequence
<220> FEATURE:
<223> OTHER INFORMATION: Synthetic

<400> SEQUENCE: 38
caggttcagc tggttcagtc tggagctgag gtgaagaagc ctggggcctc agtgaaggtc     60
tcctgcaagg cttctgatta cacctttacc acctatggta tcagctgggt gcgacaggcc    120
cctggacaag gcttgagtg gatgggatgg atcagcgcct acaatggtaa cacaaactat     180
gcacagaagg tccagggcag agtcaccatg accacagaca catccacgaa cacagcctac    240
atggaactga ggagcctgag atctgacgac acggccgtgt attattgtgc gagaggctgg    300
tacttcgatc tctggggccg tggcaccctg gtcactgtct cctca                    345
```

```
<210> SEQ ID NO 39
<211> LENGTH: 115
<212> TYPE: PRT
<213> ORGANISM: Artificial Sequence
<220> FEATURE:
<223> OTHER INFORMATION: Synthetic

<400> SEQUENCE: 39

Gln Val Gln Leu Val Gln Ser Gly Ala Glu Val Lys Lys Pro Gly Ala
1               5                   10                  15

Ser Val Lys Val Ser Cys Lys Ala Ser Asp Tyr Thr Phe Thr Thr Tyr
            20                  25                  30

Gly Ile Ser Trp Val Arg Gln Ala Pro Gly Gln Gly Leu Glu Trp Met
        35                  40                  45

Gly Trp Ile Ser Ala Tyr Asn Gly Asn Thr Asn Tyr Ala Gln Lys Val
    50                  55                  60

Gln Gly Arg Val Thr Met Thr Thr Asp Thr Ser Thr Asn Thr Ala Tyr
65              70                  75                  80

Met Glu Leu Arg Ser Leu Arg Ser Asp Asp Thr Ala Val Tyr Tyr Cys
                85                  90                  95

Ala Arg Gly Trp Tyr Phe Asp Leu Trp Gly Arg Gly Thr Leu Val Thr
            100                 105                 110

Val Ser Ser
        115
```

<210> SEQ ID NO 40

<211> LENGTH: 339
<212> TYPE: DNA
<213> ORGANISM: Artificial Sequence
<220> FEATURE:
<223> OTHER INFORMATION: Synthetic

<400> SEQUENCE: 40

```
gacatcgtga tgacccagtc tccagactcc ctggctgtgt ctctgggcga gagggccacc    60
atcaactgca gtccagcca gagtgtttta tacagctcca acaataagaa ctacttagct   120
tggtaccagc agaaaccagg acagcctcct aagctgctca tttactgggc atctacccgg   180
gaatccgggg tccctgaccg attcagtggc agcgggtctg ggacagattt cactctcacc   240
atcagcagcc tgcaggctga agatgtggca gtttattact gtcagcaata ttatagaact   300
ccgtacagtt tggccaggg gaccaagctg gagatcaaa                            339
```

<210> SEQ ID NO 41
<211> LENGTH: 113
<212> TYPE: PRT
<213> ORGANISM: Artificial Sequence
<220> FEATURE:
<223> OTHER INFORMATION: Synthetic

<400> SEQUENCE: 41

```
Asp Ile Val Met Thr Gln Ser Pro Asp Ser Leu Ala Val Ser Leu Gly
 1               5                  10                  15
Glu Arg Ala Thr Ile Asn Cys Lys Ser Ser Gln Ser Val Leu Tyr Ser
            20                  25                  30
Ser Asn Asn Lys Asn Tyr Leu Ala Trp Tyr Gln Gln Lys Pro Gly Gln
        35                  40                  45
Pro Pro Lys Leu Leu Ile Tyr Trp Ala Ser Thr Arg Glu Ser Gly Val
    50                  55                  60
Pro Asp Arg Phe Ser Gly Ser Gly Ser Gly Thr Asp Phe Thr Leu Thr
65                  70                  75                  80
Ile Ser Ser Leu Gln Ala Glu Asp Val Ala Val Tyr Tyr Cys Gln Gln
                85                  90                  95
Tyr Tyr Arg Thr Pro Tyr Ser Phe Gly Gln Gly Thr Lys Leu Glu Ile
            100                 105                 110
Lys
```

<210> SEQ ID NO 42
<211> LENGTH: 364
<212> TYPE: DNA
<213> ORGANISM: Artificial Sequence
<220> FEATURE:
<223> OTHER INFORMATION: Synthetic

<400> SEQUENCE: 42

```
caggtgcagc tggtgcagtc tggggctgag gtgaagaagc ctggggcctc agtgaaggtc    60
tcctgcaagg cttctggata caccttcacc agttatgata tcaactgggt gcgacaggcc   120
actggacaag gcttgagtg gatgggatgg atgaaccta acagtggtaa cacaggctat   180
gcacagaagt tccagggcag agtcaccatg accaggaaca cctccataag cacagcctac   240
atggagctga gcagcctgag atctgaggac acggccgtgt attactgtac gaccccaggg   300
gataagtgga actacgaata cttccaattc tggggccagg gcaccctggt caccgtctcc   360
tcag                                                                 364
```

<210> SEQ ID NO 43

```
<211> LENGTH: 121
<212> TYPE: PRT
<213> ORGANISM: Artificial Sequence
<220> FEATURE:
<223> OTHER INFORMATION: Synthetic

<400> SEQUENCE: 43

Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Ser Tyr
             20                  25                  30

Asp Ile Asn Trp Val Arg Gln Ala Thr Gly Gln Gly Leu Glu Trp Met
         35                  40                  45

Gly Trp Met Asn Pro Asn Ser Gly Asn Thr Gly Tyr Ala Gln Lys Phe
     50                  55                  60

Gln Gly Arg Val Thr Met Thr Arg Asn Thr Ser Ile Ser Thr Ala Tyr
 65                  70                  75                  80

Met Glu Leu Ser Ser Leu Arg Ser Glu Asp Thr Ala Val Tyr Tyr Cys
                 85                  90                  95

Thr Thr Pro Gly Asp Lys Trp Asn Tyr Glu Tyr Phe Gln Phe Trp Gly
            100                 105                 110

Gln Gly Thr Leu Val Thr Val Ser Ser
        115                 120

<210> SEQ ID NO 44
<211> LENGTH: 319
<212> TYPE: DNA
<213> ORGANISM: Artificial Sequence
<220> FEATURE:
<223> OTHER INFORMATION: Synthetic

<400> SEQUENCE: 44
gacatccaga tgacccagtc tccatcttcc gtgtctgcat ctgtaggaga cagagtcacc      60
atcacttgtc gggcgagtca acatattagc atctggttag cctggtatca gcagaaacca     120
gggaaagccc ctaagctcct gatctattct gcatccagtt tgcaaagtgg ggtcccatca     180
aggttcagcg gcagtggatc tgggacagat ttcactctca ccatcagcag cctgcagcct     240
gaagattttg caacttacta ttgtcaacag gcaaacagtt tccccagttt cggccctggg     300
accaaagtgg atatcaaac                                                  319

<210> SEQ ID NO 45
<211> LENGTH: 106
<212> TYPE: PRT
<213> ORGANISM: Artificial Sequence
<220> FEATURE:
<223> OTHER INFORMATION: Synthetic

<400> SEQUENCE: 45

Asp Ile Gln Met Thr Gln Ser Pro Ser Ser Val Ser Ala Ser Val Gly
 1               5                  10                  15

Asp Arg Val Thr Ile Thr Cys Arg Ala Ser Gln His Ile Ser Ile Trp
             20                  25                  30

Leu Ala Trp Tyr Gln Gln Lys Pro Gly Lys Ala Pro Lys Leu Leu Ile
         35                  40                  45

Tyr Ser Ala Ser Ser Leu Gln Ser Gly Val Pro Ser Arg Phe Ser Gly
     50                  55                  60

Ser Gly Ser Gly Thr Asp Phe Thr Leu Thr Ile Ser Ser Leu Gln Pro
 65                  70                  75                  80
```

Glu Asp Phe Ala Thr Tyr Tyr Cys Gln Gln Ala Asn Ser Phe Pro Ser
                85                  90                  95

Phe Gly Pro Gly Thr Lys Val Asp Ile Lys
            100                 105

<210> SEQ ID NO 46
<211> LENGTH: 385
<212> TYPE: DNA
<213> ORGANISM: Artificial Sequence
<220> FEATURE:
<223> OTHER INFORMATION: Synthetic

<400> SEQUENCE: 46
caggttcagc tggtgcagtc tggagctgag gtgaagaagc ctggggcctc agtgaaggtc      60
tcctgcaagg cttctggtta cacctttaat agttatggaa tcagctgggt gcgacaggcc     120
cctggacaag gcttgagtg atgggatgg atcagaactt acaatggtaa cacaaactat       180
gcacagaagc tccagggcag agtcaccatg accacagaca catccacgag cacagcctac     240
atggagctga ggagcctgag atctgacgac acggccgtgt attactgtgc gagagatgag     300
gcccgtatag tagtggctgg tacaactcct tactactacg gtatggacgt ctggggggcaa    360 gggaccacgg tcaccgtctc ctcag                                            385

<210> SEQ ID NO 47
<211> LENGTH: 128
<212> TYPE: PRT
<213> ORGANISM: Artificial Sequence
<220> FEATURE:
<223> OTHER INFORMATION: Synthetic

<400> SEQUENCE: 47

Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Asn Ser Tyr
            20                  25                  30

Gly Ile Ser Trp Val Arg Gln Ala Pro Gly Gln Gly Leu Glu Trp Met
         35                 40                  45

Gly Trp Ile Arg Thr Tyr Asn Gly Asn Thr Asn Tyr Ala Gln Lys Leu
     50                  55                  60

Gln Gly Arg Val Thr Met Thr Thr Asp Thr Ser Thr Ser Thr Ala Tyr
 65                  70                  75                  80

Met Glu Leu Arg Ser Leu Arg Ser Asp Asp Thr Ala Val Tyr Tyr Cys
                 85                 90                  95

Ala Arg Asp Glu Ala Arg Ile Val Val Ala Gly Thr Thr Pro Tyr Tyr
            100                 105                 110

Tyr Gly Met Asp Val Trp Gly Gln Gly Thr Thr Val Thr Val Ser Ser
        115                 120                 125

<210> SEQ ID NO 48
<211> LENGTH: 322
<212> TYPE: DNA
<213> ORGANISM: Artificial Sequence
<220> FEATURE:
<223> OTHER INFORMATION: Synthetic

<400> SEQUENCE: 48
gccatccaga tgacccagtc tccatcctcc ctgtctgcat ctgtaggaga cagagtcacc      60
atcacttgcc gggcaagtca ggacattaga aatgatttag ctggtatca gcagaaacca     120 gggaaagccc ctaagctcct gatctatgct gcatccagtt tacaaagtgg ggtcccatca     180

```
aggttcagcg gcagtggatc tggcacagat tcactctca ccatcagcag cctgcagcct    240
gaagattttg caacttatta ctgtctacaa gattacaatt accctcggac gttcggccaa    300
gggaccaagg tggaaatcaa ac                                             322
```

<210> SEQ ID NO 49
<211> LENGTH: 107
<212> TYPE: PRT
<213> ORGANISM: Artificial Sequence
<220> FEATURE:
<223> OTHER INFORMATION: Synthetic

<400> SEQUENCE: 49

```
Ala Ile Gln Met Thr Gln Ser Pro Ser Ser Leu Ser Ala Ser Val Gly
 1               5                  10                  15

Asp Arg Val Thr Ile Thr Cys Arg Ala Ser Gln Asp Ile Arg Asn Asp
            20                  25                  30

Leu Gly Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Asp Tyr Asn Tyr Pro Arg
                85                  90                  95

Thr Phe Gly Gln Gly Thr Lys Val Glu Ile Lys
            100                 105
```

<210> SEQ ID NO 50
<211> LENGTH: 346
<212> TYPE: DNA
<213> ORGANISM: Artificial Sequence
<220> FEATURE:
<223> OTHER INFORMATION: Synthetic

<400> SEQUENCE: 50

```
caggttcagc tggtgcagtc tggagctgag gtgaagaagc ctggggcctc agtgaaggtc     60
tcctgcaagg cttctggtta cacctttacc aactttggta tcagctgggt gcgacaggcc    120
cctggacaag gcttgagtg gatgggatgg atcagcgctt acaatggtaa cacaaactat     180
gcacagaagc tccagggcag agtcaccatg accacagaca catccacgag cacagcctac    240
atggagctga ggagcctgag atctgacgac acggccgtgt attactgtgc gagagggtgg    300
ttcttcgata tctggggccg tggcaccctg gtcactgtct cctcag                   346
```

<210> SEQ ID NO 51
<211> LENGTH: 115
<212> TYPE: PRT
<213> ORGANISM: Artificial Sequence
<220> FEATURE:
<223> OTHER INFORMATION: Synthetic

<400> SEQUENCE: 51

```
Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Asn Phe
            20                  25                  30

Gly Ile Ser Trp Val Arg Gln Ala Pro Gly Gln Gly Leu Glu Trp Met
        35                  40                  45
```

Gly Trp Ile Ser Ala Tyr Asn Gly Asn Thr Asn Tyr Ala Gln Lys Leu
            50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Gly Trp Phe Phe Asp Ile Trp Gly Arg Gly Thr Leu Val Thr
            100                 105                 110

Val Ser Ser
        115

<210> SEQ ID NO 52
<211> LENGTH: 340
<212> TYPE: DNA
<213> ORGANISM: Artificial Sequence
<220> FEATURE:
<223> OTHER INFORMATION: Synthetic

<400> SEQUENCE: 52
gacatcgtga tgacccagtc tccagactcc ctggctgtgt ctctgggcga gagggccacc      60
atcaactgca agtccagcca gagtgtttta tacagctcca acaataagaa ctatttagct     120
tggtaccagc agaaaccagg acagcctcct aagctgctca tttactgggc atctacccgg     180
gaatccgggg tccctgaccg attcagtggc agcgggtctg ggacagattt cactctcacc     240
atcagcagcc tgcaggctga agatgtggca gtttattact gtcagcaata ttatagaact     300
ccgtacactt tggccaggg gaccaagctg gagatcaaac                              340

<210> SEQ ID NO 53
<211> LENGTH: 113
<212> TYPE: PRT
<213> ORGANISM: Artificial Sequence
<220> FEATURE:
<223> OTHER INFORMATION: Synthetic

<400> SEQUENCE: 53

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
            20                  25                  30

Ser Asn Asn Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Arg Thr Pro Tyr Thr Phe Gly Gln Gly Thr Lys Leu Glu Ile
            100                 105                 110

Lys

<210> SEQ ID NO 54
<211> LENGTH: 346
<212> TYPE: DNA
<213> ORGANISM: Artificial Sequence
<220> FEATURE:
<223> OTHER INFORMATION: Synthetic

<400> SEQUENCE: 54

```
caggttcagc tggtgcagtc tggagctgag gtgaagaagc ctggggcctc agtgaaggtc    60
tcctgcaagg cttctggtta caactttatc agctatggta tcagctgggt gcgacaggcc   120
cctggacaag gcttgagtg gatgggatgg atcaccactt acaatggtaa cacaaactat    180
gcacagaagc tccagggcag agtcaccatg accacagaca catccacgag cacagcctac   240
atggagctga ggagcctgag atctgacgac acggccgtgt attactgtgc gagagggtgg   300
tacttcgatc tctggggccg tggcaccctg gtcactgtct cctcag                  346
```

<210> SEQ ID NO 55
<211> LENGTH: 115
<212> TYPE: PRT
<213> ORGANISM: Artificial Sequence
<220> FEATURE:
<223> OTHER INFORMATION: Synthetic

<400> SEQUENCE: 55

```
Gln Val Gln Leu Val Gln Ser Gly Ala Glu Val Lys Lys Pro Gly Ala
  1               5                  10                  15

Ser Val Lys Val Ser Cys Lys Ala Ser Gly Tyr Asn Phe Ile Ser Tyr
             20                  25                  30

Gly Ile Ser Trp Val Arg Gln Ala Pro Gly Gln Gly Leu Glu Trp Met
         35                  40                  45

Gly Trp Ile Thr Thr Tyr Asn Gly Asn Thr Asn Tyr Ala Gln Lys Leu
     50                  55                  60

Gln Gly Arg Val Thr Met Thr Thr Asp Thr Ser Thr Ser Thr Ala Tyr
 65                  70                  75                  80

Met Glu Leu Arg Ser Leu Arg Ser Asp Asp Thr Ala Val Tyr Tyr Cys
                 85                  90                  95

Ala Arg Gly Trp Tyr Phe Asp Leu Trp Gly Arg Gly Thr Leu Val Thr
            100                 105                 110

Val Ser Ser
        115
```

<210> SEQ ID NO 56
<211> LENGTH: 340
<212> TYPE: DNA
<213> ORGANISM: Artificial Sequence
<220> FEATURE:
<223> OTHER INFORMATION: Synthetic

<400> SEQUENCE: 56

```
gacatcgtga tgacccagtc tccagactcc ctggctgtgt ctctgggcga gagggccacc    60
atcaactgca gtccagcca gagtgttttt tacagctcca acaataagaa ctacttagct   120
tggtaccagc agaaaccagg acagcctcct aagctgctca tttactgggc atctacccgg   180
gaatccgggg tccctgaccg attcagtggc agcgggtctg ggacagattt cactctcacc   240
atcagcagcc tgcaggctga agatgtggca gtttattact gtcagcaata ttatcgtact   300
ccgtacactt ttggccaggg gaccaagctg gagatcaaac                         340
```

<210> SEQ ID NO 57
<211> LENGTH: 113
<212> TYPE: PRT
<213> ORGANISM: Artificial Sequence
<220> FEATURE:
<223> OTHER INFORMATION: Synthetic

<400> SEQUENCE: 57

```
Asp Ile Val Met Thr Gln Ser Pro Asp Ser Leu Ala Val Ser Leu Gly
 1               5                  10                  15

Glu Arg Ala Thr Ile Asn Cys Lys Ser Ser Gln Ser Val Phe Tyr Ser
             20                  25                  30

Ser Asn Asn Lys Asn Tyr Leu Ala Trp Tyr Gln Lys Pro Gly Gln
         35                  40                  45

Pro Pro Lys Leu Leu Ile Tyr Trp Ala Ser Thr Arg Glu Ser Gly Val
 50                  55                  60

Pro Asp Arg Phe Ser Gly Ser Gly Ser Gly Thr Asp Phe Thr Leu Thr
 65                  70                  75                  80

Ile Ser Ser Leu Gln Ala Glu Asp Val Ala Val Tyr Tyr Cys Gln Gln
                 85                  90                  95

Tyr Tyr Arg Thr Pro Tyr Thr Phe Gly Gln Gly Thr Lys Leu Glu Ile
            100                 105                 110

Lys
```

<210> SEQ ID NO 58
<211> LENGTH: 346
<212> TYPE: DNA
<213> ORGANISM: Artificial Sequence
<220> FEATURE:
<223> OTHER INFORMATION: Synthetic

<400> SEQUENCE: 58

```
caggttcagc tggtgcagtc tggagctgag gtgaagaagc ctggggcctc agtgaaggtc      60
tcctgcaagg cttctggtta cacctttacc agctatggta tcagctgggt gcgacaggcc     120
cctggacaag gcttgagtg gatgggatgg atcagcgctt ataatggaaa cacaaactat      180
gcacagaagc tccagggcag agtcaccatg accacagaca catccacgag cacagcctac     240
atggagctga ggagcctgag atctgacgac acggccgtgt attactgtgc gagggctgg      300 tacttcgctc tctggggccg tggcaccctg gtcactgtct cctcag                    346
```

<210> SEQ ID NO 59
<211> LENGTH: 115
<212> TYPE: PRT
<213> ORGANISM: Artificial Sequence
<220> FEATURE:
<223> OTHER INFORMATION: Synthetic

<400> SEQUENCE: 59

```
Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Ser Tyr
             20                  25                  30

Gly Ile Ser Trp Val Arg Gln Ala Pro Gly Gln Gly Leu Glu Trp Met
         35                  40                  45

Gly Trp Ile Ser Ala Tyr Asn Gly Asn Thr Asn Tyr Ala Gln Lys Leu
 50                  55                  60

Gln Gly Arg Val Thr Met Thr Thr Asp Thr Ser Thr Ser Thr Ala Tyr
 65                  70                  75                  80

Met Glu Leu Arg Ser Leu Arg Ser Asp Asp Thr Ala Val Tyr Tyr Cys
                 85                  90                  95

Ala Arg Gly Trp Tyr Phe Ala Leu Trp Gly Arg Gly Thr Leu Val Thr
            100                 105                 110

Val Ser Ser
            115
```

<210> SEQ ID NO 60
<211> LENGTH: 340
<212> TYPE: DNA
<213> ORGANISM: Artificial Sequence
<220> FEATURE:
<223> OTHER INFORMATION: Synthetic

<400> SEQUENCE: 60

| | | | | | |
|---|---|---|---|---|---|
| gacatcgtga | tgacccagtc | tccagactcc | ctggctgtgt | ctctgggcga | gagggccacc | 60 |
| atcaactgca | agtccagcca | gagtgtttta | tacagctcca | acaataggaa | ctacttagct | 120 |
| tggtaccagc | agaaaccagg | acagcctcct | aagctgctca | tttactgggc | atctacccgg | 180 |
| gaatccgggg | tccctgaccg | attcagtggc | agcgggtctg | ggacagattt | cactctcacc | 240 |
| atcagcagcc | tgcaggctga | agatgtggca | gtttattact | gtcagcaatt | ttatcgtact | 300 |
| ccgtacactt | ttggccaggg | gaccaagctg | gagatcaaac | | | 340 |

<210> SEQ ID NO 61
<211> LENGTH: 113
<212> TYPE: PRT
<213> ORGANISM: Artificial Sequence
<220> FEATURE:
<223> OTHER INFORMATION: Synthetic

<400> SEQUENCE: 61

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
            20                  25                  30

Ser Asn Asn Arg Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Phe Tyr Arg Thr Pro Tyr Thr Phe Gly Gln Gly Thr Lys Leu Glu Ile
            100                 105                 110

Lys

<210> SEQ ID NO 62
<211> LENGTH: 346
<212> TYPE: DNA
<213> ORGANISM: Artificial Sequence
<220> FEATURE:
<223> OTHER INFORMATION: Synthetic

<400> SEQUENCE: 62

| | | | | | |
|---|---|---|---|---|---|
| caggttcagc | tggtgcagtc | tggagctgag | gtgaagaagc | ctggggcctc | agtgaaggtc | 60 |
| tcctgcaagg | cttctggtta | cacctttacc | agctatggta | tcagctgggt | gcgacaggcc | 120 |
| cctggacaag | ggcttgagtg | gatgggatgg | atcagcgttt | acaatggtaa | cacaaactat | 180 |
| gcacagaagc | tccagggcag | agtcaccatg | accacagaca | catccacgag | cacagcctac | 240 |
| atggagctga | ggagcctgag | atctgacgac | acggccgtgt | attactgtgc | gagagggtgg | 300 |
| tacttcgatc | tctggggccg | tggcaccctg | gtcactgtct | cctcag | | 346 |

<210> SEQ ID NO 63

<211> LENGTH: 115
<212> TYPE: PRT
<213> ORGANISM: Artificial Sequence
<220> FEATURE:
<223> OTHER INFORMATION: Synthetic

<400> SEQUENCE: 63

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Gly Ile Ser Trp Val Arg Gln Ala Pro Gly Gln Gly Leu Glu Trp Met
        35                  40                  45

Gly Trp Ile Ser Val Tyr Asn Gly Asn Thr Asn Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Gly Trp Tyr Phe Asp Leu Trp Gly Arg Gly Thr Leu Val Thr
            100                 105                 110

Val Ser Ser
        115

<210> SEQ ID NO 64
<211> LENGTH: 340
<212> TYPE: DNA
<213> ORGANISM: Artificial Sequence
<220> FEATURE:
<223> OTHER INFORMATION: Synthetic

<400> SEQUENCE: 64
gacatcgtga tgacccagtc tccagactcc ctggctgtgt ctctgggcga gagggccacc      60
atcaactgca agtccagcca gactgtttta tacagctcca acaataagac ctacttagct     120
tggtaccagc agaaaccagg acagcctcct aagctgctca tttactgggc atctacccgg     180
gaatccgggg tccctgaccg attcagtggc agcgggtctg ggacagattt cactctcacc     240
atcagcagcc tgcaggctga agatgtggca gtttattact gtcagcaata ttatcgtact     300
ccgtacactt ttggccaggg gaccaagctg gagatcaaac                           340

<210> SEQ ID NO 65
<211> LENGTH: 113
<212> TYPE: PRT
<213> ORGANISM: Artificial Sequence
<220> FEATURE:
<223> OTHER INFORMATION: Synthetic

<400> SEQUENCE: 65

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Thr Val Leu Tyr Ser
            20                  25                  30

Ser Asn Asn Lys Thr Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Arg Thr Pro Tyr Thr Phe Gly Gln Gly Thr Lys Leu Glu Ile
            100                 105                 110

Lys

<210> SEQ ID NO 66
<211> LENGTH: 346
<212> TYPE: DNA
<213> ORGANISM: Artificial Sequence
<220> FEATURE:
<223> OTHER INFORMATION: Synthetic

<400> SEQUENCE: 66
caggttcagc tggtgcagtc tggagctgag gtgaagaagc ctggggcctc agtgaaggtc      60
tcctgcaagg cttctggtta cacctttagc agctatggta tcagctgggt gcgacaggcc     120
cctggacaag gcttgagtg gatgggatgg atcagcgttt acaatggtaa cacaaactat     180
gcacagaagc tccagggcag agtcaccatg accacagaca catccacgag cacagcctac     240
atggagctga ggagcctgag atctgacgac acggccgtgt attactgtac gagagggtgg     300
tatttcgatc tctggggccg tggcaccctg gtcactgtct cctcag                   346

<210> SEQ ID NO 67
<211> LENGTH: 115
<212> TYPE: PRT
<213> ORGANISM: Artificial Sequence
<220> FEATURE:
<223> OTHER INFORMATION: Synthetic

<400> SEQUENCE: 67

Gln Val Gln Leu Val Gln Ser Gly Ala Glu Val Lys Lys Pro Gly Ala
  1               5                  10                  15

Ser Val Lys Val Ser Cys Lys Ala Ser Gly Tyr Thr Phe Ser Ser Tyr
             20                  25                  30

Gly Ile Ser Trp Val Arg Gln Ala Pro Gly Gln Gly Leu Glu Trp Met
         35                  40                  45

Gly Trp Ile Ser Val Tyr Asn Gly Asn Thr Asn Tyr Ala Gln Lys Leu
     50                  55                  60

Gln Gly Arg Val Thr Met Thr Thr Asp Thr Ser Thr Ser Thr Ala Tyr
 65                  70                  75                  80

Met Glu Leu Arg Ser Leu Arg Ser Asp Asp Thr Ala Val Tyr Tyr Cys
                 85                  90                  95

Thr Arg Gly Trp Tyr Phe Asp Leu Trp Gly Arg Gly Thr Leu Val Thr
            100                 105                 110

Val Ser Ser
        115

<210> SEQ ID NO 68
<211> LENGTH: 340
<212> TYPE: DNA
<213> ORGANISM: Artificial Sequence
<220> FEATURE:
<223> OTHER INFORMATION: Synthetic

<400> SEQUENCE: 68
gacatcgtga tgacccagtc tccagactcc ctggctgtgt ctctgggcga gagggccacc      60
atcaactgca gtccagcca gactgtttta tacagctcca acaataagaa ctacttagct     120
tggtaccagc agaaaccagg acagcctcct aagctgctca tttactggtc atctacccgg     180

```
gaatccgggg tccctgaccg attcagtggc agcgggtctg ggacagattt cactctcacc      240
atcagcagcc tgcaggctga agatgtggca gtttattact gtcagcaata ttatcgtact      300
ccgtacactt ttggccaggg gaccaagctg gagatcaaac                             340
```

<210> SEQ ID NO 69
<211> LENGTH: 113
<212> TYPE: PRT
<213> ORGANISM: Artificial Sequence
<220> FEATURE:
<223> OTHER INFORMATION: Synthetic

<400> SEQUENCE: 69

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Thr Val Leu Tyr Ser
            20                  25                  30

Ser Asn Asn Lys Asn Tyr Leu Ala Trp Tyr Gln Gln Lys Pro Gly Gln
        35                  40                  45

Pro Pro Lys Leu Leu Ile Tyr Trp Ser Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Arg Thr Pro Tyr Thr Phe Gly Gln Gly Thr Lys Leu Glu Ile
            100                 105                 110

Lys

<210> SEQ ID NO 70
<211> LENGTH: 355
<212> TYPE: DNA
<213> ORGANISM: Artificial Sequence
<220> FEATURE:
<223> OTHER INFORMATION: Synthetic

<400> SEQUENCE: 70

```
caggtgcaac tggtgcagtc tggggctgag gtgaagaagc ctggggcctc agtgaaggtc      60
tcctgcaagg cttctggata caccttcacc ggctactata tgcactgggt gcgacaggcc     120
cctggacaag gcttgagtg gatgggatgg atcaaccta acagtggtgg cacaaactat       180
gcacagaagt tcagggcag ggtcaccatg accaggaca cgtccatcag cacagcctac       240
atggagctga gcaggctgag atctgacgac acggccgtgt attactgtgc gcgagatatg     300
ggggacctat tttttgacta ctggggccag ggaaccctgg tcaccgtctc ctcag          355
```

<210> SEQ ID NO 71
<211> LENGTH: 118
<212> TYPE: PRT
<213> ORGANISM: Artificial Sequence
<220> FEATURE:
<223> OTHER INFORMATION: Synthetic

<400> SEQUENCE: 71

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met

```
                    35                  40                  45
Gly Trp Ile Asn Pro Asn Ser Gly Gly Thr Asn Tyr Ala Gln Lys Phe
 50                  55                  60

Gln Gly Arg Val Thr Met Thr Arg Asp Thr Ser Ile Ser Thr Ala Tyr
 65                  70                  75                  80

Met Glu Leu Ser Arg Leu Arg Ser Asp Asp Thr Ala Val Tyr Tyr Cys
                 85                  90                  95

Ala Arg Asp Met Gly Asp Leu Phe Phe Asp Tyr Trp Gly Gln Gly Thr
             100                 105                 110

Leu Val Thr Val Ser Ser
            115

<210> SEQ ID NO 72
<211> LENGTH: 337
<212> TYPE: DNA
<213> ORGANISM: Artificial Sequence
<220> FEATURE:
<223> OTHER INFORMATION: Synthetic

<400> SEQUENCE: 72
gacatcgtga tgacccagtc tccagactcc ctggctgtgt ctctgggcga gagggccacc     60
atcaactgca gtccagcca gagtgttttt tacagctcca acaataagaa ctacttagct    120
tggtaccagc agaaaccagg acagcctcct aagctgctca tttactgggc atctacccgg    180
gaatccgggg tccctgaccg attcagtggc agcgggtctg ggacagattt cactctcacc    240
atcagcagcc tgcaggctga agatgtggca gtttattact gtcaacaata tttttattact    300 tggacgttcg gccaagggac caaggtggaa atcaaac                              337

<210> SEQ ID NO 73
<211> LENGTH: 112
<212> TYPE: PRT
<213> ORGANISM: Artificial Sequence
<220> FEATURE:
<223> OTHER INFORMATION: Synthetic

<400> SEQUENCE: 73

Asp Ile Val Met Thr Gln Ser Pro Asp Ser Leu Ala Val Ser Leu Gly
  1               5                  10                  15

Glu Arg Ala Thr Ile Asn Cys Lys Ser Ser Gln Ser Val Phe Tyr Ser
             20                  25                  30

Ser Asn Asn Lys Asn Tyr Leu Ala Trp Tyr Gln Gln Lys Pro Gly Gln
         35                  40                  45

Pro Pro Lys Leu Leu Ile Tyr Trp Ala Ser Thr Arg Glu Ser Gly Val
 50                  55                  60

Pro Asp Arg Phe Ser Gly Ser Gly Ser Gly Thr Asp Phe Thr Leu Thr
 65                  70                  75                  80

Ile Ser Ser Leu Gln Ala Glu Asp Val Ala Val Tyr Tyr Cys Gln Gln
                 85                  90                  95

Tyr Phe Ile Thr Trp Thr Phe Gly Gln Gly Thr Lys Val Glu Ile Lys
             100                 105                 110

<210> SEQ ID NO 74
<211> LENGTH: 358
<212> TYPE: DNA
<213> ORGANISM: Artificial Sequence
<220> FEATURE:
<223> OTHER INFORMATION: Synthetic

<400> SEQUENCE: 74
```

```
caggtacagc tgcagcagtc aggtccagga ctggtgaagc cctcgcagac cctctcactc     60
acctgtgcca tctccgggga cagtgtctct acctacagtg ctgcttggaa ctggatcagg    120
cagtccccat cgagaggcct tgagtggctg gaaggacat actacaggtc cgagtggtat     180
aatgattatg cagtatctgt gaaaagtcga ataaccatca acccagacac atccaagaac    240
cagttctccc tgcagctgaa ctctgtgact cccgaggaca cggctgtgta ttactgtgtg    300
agagagggag atgcttttga tatctggggc caagggacaa tggtcaccgt ctcttcag     358
```

<210> SEQ ID NO 75
<211> LENGTH: 119
<212> TYPE: PRT
<213> ORGANISM: Artificial Sequence
<220> FEATURE:
<223> OTHER INFORMATION: Synthetic

<400> SEQUENCE: 75

```
Gln Val Gln Leu Gln Gln Ser Gly Pro Gly Leu Val Lys Pro Ser Gln
 1               5                   10                  15

Thr Leu Ser Leu Thr Cys Ala Ile Ser Gly Asp Ser Val Ser Thr Tyr
             20                  25                  30

Ser Ala Ala Trp Asn Trp Ile Arg Gln Ser Pro Ser Arg Gly Leu Glu
         35                  40                  45

Trp Leu Gly Arg Thr Tyr Tyr Arg Ser Glu Trp Tyr Asn Asp Tyr Ala
     50                  55                  60

Val Ser Val Lys Ser Arg Ile Thr Ile Asn Pro Asp Thr Ser Lys Asn
 65                  70                  75                  80

Gln Phe Ser Leu Gln Leu Asn Ser Val Thr Pro Glu Asp Thr Ala Val
                 85                  90                  95

Tyr Tyr Cys Val Arg Glu Gly Asp Ala Phe Asp Ile Trp Gly Gln Gly
            100                 105                 110

Thr Met Val Thr Val Ser Ser
        115
```

<210> SEQ ID NO 76
<211> LENGTH: 322
<212> TYPE: DNA
<213> ORGANISM: Artificial Sequence
<220> FEATURE:
<223> OTHER INFORMATION: Synthetic

<400> SEQUENCE: 76

```
gaaattgtgt tgacacagtc tccagccacc ctgtctttgt ctccagggga aagagccacc     60
ctctcctgca gggccagtca gagtgttagc agctacttag cctggtacca acagaaacct    120
ggccaggctc ccaggctcct catctatgat gcgtctaaca gggccactgg catcccagcc    180
aggttcagtg gcagtgggtc tgggacagac ttcactctca ccatcagcag cctagagcct    240
gaagattttg cagtttatta ctgtcagcag cgtggcaatt ggcctcctac tttcggcgga    300
gggaccaagg tggagatcaa ac                                             322
```

<210> SEQ ID NO 77
<211> LENGTH: 107
<212> TYPE: PRT
<213> ORGANISM: Artificial Sequence
<220> FEATURE:
<223> OTHER INFORMATION: Synthetic

<400> SEQUENCE: 77

```
Glu Ile Val Leu Thr Gln Ser Pro Ala Thr Leu Ser Leu Ser Pro Gly
 1               5                  10                  15

Glu Arg Ala Thr Leu Ser Cys Arg Ala Ser Gln Ser Val Ser Ser Tyr
                20                  25                  30

Leu Ala Trp Tyr Gln Gln Lys Pro Gly Gln Ala Pro Arg Leu Leu Ile
            35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Gly Asn Trp Pro Pro
                85                  90                  95

Thr Phe Gly Gly Gly Thr Lys Val Glu Ile Lys
            100                 105
```

```
<210> SEQ ID NO 78
<211> LENGTH: 346
<212> TYPE: DNA
<213> ORGANISM: Artificial Sequence
<220> FEATURE:
<223> OTHER INFORMATION: Synthetic

<400> SEQUENCE: 78
caggttcagc tggtgcagtc tggagctgag gtgaagaagc ctggggcctc agtgaaggtc     60
tcctgcaagg cttctgatta cacctttacc acctatggta tcagctgggt gcgacaggcc    120
cctggacaag gcttgagtg gatgggatgg atcagcgcct acaatggtaa cacaaactat    180
gcacagaagc tccagggcag agtcaccatg accacagaca catccacgag cacagcctac    240
atggagctga ggagcctgag atctgacgac acggccgtgt attactgtgc gagaggctgg    300
tacttcgatc tctggggccg tggcaccctg gtcactgtct cctcag                  346
```

```
<210> SEQ ID NO 79
<211> LENGTH: 115
<212> TYPE: PRT
<213> ORGANISM: Artificial Sequence
<220> FEATURE:
<223> OTHER INFORMATION: Synthetic

<400> SEQUENCE: 79

Gln Val Gln Leu Val Gln Ser Gly Ala Glu Val Lys Lys Pro Gly Ala
 1               5                  10                  15

Ser Val Lys Val Ser Cys Lys Ala Ser Asp Tyr Thr Phe Thr Thr Tyr
                20                  25                  30

Gly Ile Ser Trp Val Arg Gln Ala Pro Gly Gln Gly Leu Glu Trp Met
            35                  40                  45

Gly Trp Ile Ser Ala Tyr Asn Gly Asn Thr Asn Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Gly Trp Tyr Phe Asp Leu Trp Gly Arg Gly Thr Leu Val Thr
            100                 105                 110

Val Ser Ser
        115
```

```
<210> SEQ ID NO 80
```

-continued

```
<211> LENGTH: 340
<212> TYPE: DNA
<213> ORGANISM: Artificial Sequence
<220> FEATURE:
<223> OTHER INFORMATION: Synthetic

<400> SEQUENCE: 80
gacatcgtga tgacccagtc tccagactcc ctggctgtgt ctctgggcga gagggccacc       60
atcaactgca gtccagcca gagtgtttta tacagctcca acaataagaa ctacttagct      120
tggtaccagc agaaaccagg acagcctcct aagctgctca tttactgggc atctacccgg     180
gaatccgggg tccctgaccg attcagtggc agcgggtctg ggacagattt cactctcacc     240
atcagcagcc tgcaggctga agatgtggca gtttattact gtcagcaata ttatagaact     300
ccgtacagtt ttggccaggg gaccaagctg gagatcaaac                           340

<210> SEQ ID NO 81
<211> LENGTH: 113
<212> TYPE: PRT
<213> ORGANISM: Artificial Sequence
<220> FEATURE:
<223> OTHER INFORMATION: Synthetic

<400> SEQUENCE: 81

Asp Ile Val Met Thr Gln Ser Pro Asp Ser Leu Ala Val Ser Leu Gly
 1               5                  10                  15

Glu Arg Ala Thr Ile Asn Cys Lys Ser Ser Gln Ser Val Leu Tyr Ser
            20                  25                  30

Ser Asn Asn Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Arg Thr Pro Tyr Ser Phe Gly Gln Gly Thr Lys Leu Glu Ile
            100                 105                 110

Lys

<210> SEQ ID NO 82
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: VARIANT
<222> LOCATION: (1)...(10)
<223> OTHER INFORMATION: Xaa = Any amino acid

<400> SEQUENCE: 82

Xaa Xaa Xaa Xaa Xaa Xaa Xaa Xaa Xaa Xaa
 1               5                  10

<210> SEQ ID NO 83
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: VARIANT
```

```
<222> LOCATION: (1)...(9)
<223> OTHER INFORMATION: Xaa = Any amino acid

<400> SEQUENCE: 83

Xaa Xaa Xaa Xaa Xaa Xaa Xaa Xaa Xaa
 1               5

<210> SEQ ID NO 84
<211> LENGTH: 21
<212> TYPE: PRT
<213> ORGANISM: Artificial Sequence
<220> FEATURE:
<223> OTHER INFORMATION: Synthetic
<220> FEATURE:
<221> NAME/KEY: VARIANT
<222> LOCATION: (1)...(21)
<223> OTHER INFORMATION: Xaa = Any amino acid

<400> SEQUENCE: 84

Xaa Xaa Xaa Xaa Xaa Xaa Xaa Xaa Xaa Xaa Xaa Xaa Xaa Xaa Xaa Xaa
 1               5                  10                  15

Xaa Xaa Xaa Xaa Xaa
            20

<210> SEQ ID NO 85
<211> LENGTH: 12
<212> TYPE: PRT
<213> ORGANISM: Artificial Sequence
<220> FEATURE:
<223> OTHER INFORMATION: Synthetic
<220> FEATURE:
<221> NAME/KEY: VARIANT
<222> LOCATION: (1)...(12)
<223> OTHER INFORMATION: Xaa = Any amino acid

<400> SEQUENCE: 85

Xaa Xaa Xaa Xaa Xaa Xaa Xaa Xaa Xaa Xaa Xaa Xaa
 1               5                  10

<210> SEQ ID NO 86
<211> LENGTH: 3
<212> TYPE: PRT
<213> ORGANISM: Artificial Sequence
<220> FEATURE:
<223> OTHER INFORMATION: Synthetic
<220> FEATURE:
<221> NAME/KEY: VARIANT
<222> LOCATION: (1)...(3)
<223> OTHER INFORMATION: Xaa = Any amino acid

<400> SEQUENCE: 86

Xaa Xaa Xaa
 1

<210> SEQ ID NO 87
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: VARIANT
<222> LOCATION: (1)...(9)
<223> OTHER INFORMATION: Xaa = Any amino acid

<400> SEQUENCE: 87

Xaa Xaa Xaa Xaa Xaa Xaa Xaa Xaa Xaa
 1               5
```

<210> SEQ ID NO 88
<211> LENGTH: 448
<212> TYPE: PRT
<213> ORGANISM: Artificial Sequence
<220> FEATURE:
<223> OTHER INFORMATION: Synthetic

<400> SEQUENCE: 88

Gln Val Gln Leu Val Gln Ser Gly Ala Glu Val Lys Lys Pro Gly Ala
1               5                   10                  15

Ser Val Arg Val Ser Cys Lys Ala Ser Gly Tyr Thr Phe Thr Ser Tyr
            20                  25                  30

Asp Ile Asn Trp Val Arg Gln Ala Thr Gly Gln Gly Leu Glu Tyr Met
        35                  40                  45

Gly Trp Met Asn Pro Asn Ser Gly Asn Thr Gly Tyr Ala Gln Lys Phe
    50                  55                  60

Gln Gly Arg Val Ser Leu Thr Arg Asp Thr Ser Ile Ser Thr Ala Tyr
65                  70                  75                  80

Met Asp Leu Asn Ser Leu Arg Ser Glu Asp Thr Ala Val Tyr Tyr Cys
                85                  90                  95

Thr Thr Pro Gly Asp Lys Trp Asn Tyr Glu Tyr Phe Gln Phe Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Cys Ser Arg Ser Thr Ser Glu Ser Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Lys Thr Tyr Thr Cys Asn Val Asp His
        195                 200                 205

Lys Pro Ser Asn Thr Lys Val Asp Lys Arg Val Glu Ser Lys Tyr Gly
    210                 215                 220

Pro Pro Cys Pro Ser Cys Pro Ala Pro Glu Phe Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser Gln Glu Asp Pro
            260                 265                 270

Glu Val Gln Phe Asn Trp Tyr Val Asp Gly Val Glu Val His Asn Ala
        275                 280                 285

Lys Thr Lys Pro Arg Glu Glu Gln Phe Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Gly Leu Pro Ser Ser Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Gln Glu Glu Met Thr Lys Asn Gln Val Ser Leu Thr Cys
        355                 360                 365

```
Leu Val Lys Gly Phe Tyr Pro Ser Asp Ile Ala Val Glu Trp Glu Ser
        370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Arg Leu Thr Val Asp Lys Ser
                405                 410                 415

Arg Trp Gln Glu Gly Asn Val Phe Ser Cys Ser Val Met His Glu Ala
            420                 425                 430

Leu His Asn His Tyr Thr Gln Lys Ser Leu Ser Leu Ser Leu Gly Lys
        435                 440                 445

<210> SEQ ID NO 89
<211> LENGTH: 442
<212> TYPE: PRT
<213> ORGANISM: Artificial Sequence
<220> FEATURE:
<223> OTHER INFORMATION: Synthetic

<400> SEQUENCE: 89

Gln Val Gln Leu Val Gln Ser Gly Ala Glu Val Lys Lys Pro Gly Ala
1               5                   10                  15

Ser Met Lys Val Ser Cys Lys Ala Ser Gly Tyr Thr Phe Thr Asn Phe
            20                  25                  30

Gly Ile Ser Trp Val Arg Gln Ala Pro Gly Gln Gly Leu Glu Trp Met
        35                  40                  45

Gly Trp Ile Ser Ala Tyr Asn Gly Asn Thr Asn Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Thr Ala Val Tyr Tyr Cys
                85                  90                  95

Ala Arg Gly Trp Phe Phe Asp Ile Trp Gly Arg Gly Thr Leu Val Thr
            100                 105                 110

Val Ser Ser Ala Ser Thr Lys Gly Pro Ser Val Phe Pro Leu Ala Pro
        115                 120                 125

Cys Ser Arg Ser Thr Ser Glu Ser Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Lys Thr Tyr Thr Cys Asn Val Asp His Lys Pro Ser Asn Thr Lys
        195                 200                 205

Val Asp Lys Arg Val Glu Ser Lys Tyr Gly Pro Pro Cys Pro Ser Cys
    210                 215                 220

Pro Ala Pro Glu Phe Leu Gly Gly Pro Ser Val Phe Leu Phe Pro Pro
225                 230                 235                 240

Lys Pro Lys Asp Thr Leu Met Ile Ser Arg Thr Pro Glu Val Thr Cys
                245                 250                 255

Val Val Val Asp Val Ser Gln Glu Asp Pro Glu Val Gln Phe Asn Trp
            260                 265                 270

Tyr Val Asp Gly Val Glu Val His Asn Ala Lys Thr Lys Pro Arg Glu
        275                 280                 285
```

```
Glu Gln Phe Asn Ser Thr Tyr Arg Val Val Ser Val Leu Thr Val Leu
    290                 295                 300

His Gln Asp Trp Leu Asn Gly Lys Glu Tyr Lys Cys Lys Val Ser Asn
305                 310                 315                 320

Lys Gly Leu Pro Ser Ser Ile Glu Lys Thr Ile Ser Lys Ala Lys Gly
                325                 330                 335

Gln Pro Arg Glu Pro Gln Val Tyr Thr Leu Pro Pro Ser Gln Glu Glu
            340                 345                 350

Met Thr Lys Asn Gln Val Ser Leu Thr Cys Leu Val Lys Gly Phe Tyr
        355                 360                 365

Pro Ser Asp Ile Ala Val Glu Trp Glu Ser Asn Gly Gln Pro Glu Asn
    370                 375                 380

Asn Tyr Lys Thr Thr Pro Pro Val Leu Asp Ser Asp Gly Ser Phe Phe
385                 390                 395                 400

Leu Tyr Ser Arg Leu Thr Val Asp Lys Ser Arg Trp Gln Glu Gly Asn
                405                 410                 415

Val Phe Ser Cys Ser Val Met His Glu Ala Leu His Asn His Tyr Thr
            420                 425                 430

Gln Lys Ser Leu Ser Leu Ser Leu Gly Lys
        435                 440

<210> SEQ ID NO 90
<211> LENGTH: 442
<212> TYPE: PRT
<213> ORGANISM: Artificial Sequence
<220> FEATURE:
<223> OTHER INFORMATION: Synthetic

<400> SEQUENCE: 90

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Asn Phe Ile Ser Tyr
            20                  25                  30

Gly Ile Ser Trp Val Arg Gln Ala Pro Gly Gln Gly Leu Glu Trp Met
        35                  40                  45

Gly Trp Ile Thr Thr Tyr Asn Gly Asn Thr Asn Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Gly Trp Tyr Phe Asp Leu Trp Gly Arg Gly Thr Leu Val Thr
            100                 105                 110

Val Ser Ser Ala Ser Thr Lys Gly Pro Ser Val Phe Pro Leu Ala Pro
        115                 120                 125

Cys Ser Arg Ser Thr Ser Glu Ser Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Lys Thr Tyr Thr Cys Asn Val Asp His Lys Pro Ser Asn Thr Lys
        195                 200                 205
```

```
Val Asp Lys Arg Val Glu Ser Lys Tyr Gly Pro Pro Cys Pro Ser Cys
    210                 215                 220

Pro Ala Pro Glu Phe Leu Gly Gly Pro Ser Val Phe Leu Phe Pro Pro
225                 230                 235                 240

Lys Pro Lys Asp Thr Leu Met Ile Ser Arg Thr Pro Glu Val Thr Cys
                245                 250                 255

Val Val Val Asp Val Ser Gln Glu Asp Pro Glu Val Gln Phe Asn Trp
            260                 265                 270

Tyr Val Asp Gly Val Glu Val His Asn Ala Lys Thr Lys Pro Arg Glu
        275                 280                 285

Glu Gln Phe Asn Ser Thr Tyr Arg Val Val Ser Val Leu Thr Val Leu
    290                 295                 300

His Gln Asp Trp Leu Asn Gly Lys Glu Tyr Lys Cys Lys Val Ser Asn
305                 310                 315                 320

Lys Gly Leu Pro Ser Ser Ile Glu Lys Thr Ile Ser Lys Ala Lys Gly
                325                 330                 335

Gln Pro Arg Glu Pro Gln Val Tyr Thr Leu Pro Pro Ser Gln Glu Glu
            340                 345                 350

Met Thr Lys Asn Gln Val Ser Leu Thr Cys Leu Val Lys Gly Phe Tyr
        355                 360                 365

Pro Ser Asp Ile Ala Val Glu Trp Glu Ser Asn Gly Gln Pro Glu Asn
    370                 375                 380

Asn Tyr Lys Thr Thr Pro Pro Val Leu Asp Ser Asp Gly Ser Phe Phe
385                 390                 395                 400

Leu Tyr Ser Arg Leu Thr Val Asp Lys Ser Arg Trp Gln Glu Gly Asn
                405                 410                 415

Val Phe Ser Cys Ser Val Met His Glu Ala Leu His Asn His Tyr Thr
            420                 425                 430

Gln Lys Ser Leu Ser Leu Ser Leu Gly Lys
        435                 440

<210> SEQ ID NO 91
<211> LENGTH: 455
<212> TYPE: PRT
<213> ORGANISM: Artificial Sequence
<220> FEATURE:
<223> OTHER INFORMATION: Synthetic

<400> SEQUENCE: 91

Gln Val Gln Leu Val Gln Ser Gly Ala Glu Val Lys Lys Pro Gly Ala
  1               5                  10                  15

Ser Val Lys Val Ser Cys Lys Ala Ser Gly Tyr Thr Phe Asn Ser Tyr
             20                  25                  30

Gly Ile Ser Trp Val Arg Gln Ala Pro Gly Gln Gly Leu Glu Trp Met
         35                  40                  45

Gly Trp Ile Arg Thr Tyr Asn Gly Asn Thr Asn Tyr Ala Gln Lys Leu
     50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                 85                  90                  95

Ala Arg Asp Glu Ala Arg Ile Val Val Ala Gly Thr Thr Pro Tyr Tyr
            100                 105                 110

Tyr Gly Met Asp Val Trp Gly Gln Gly Thr Thr Val Thr Val Ser Ser
        115                 120                 125
```

```
Ala Ser Thr Lys Gly Pro Ser Val Phe Pro Leu Ala Pro Cys Ser Arg
        130             135             140

Ser Thr Ser Glu Ser Thr Ala Ala Leu Gly Cys Leu Val Lys Asp Tyr
145             150             155             160

Phe Pro Glu Pro Val Thr Val Ser Trp Asn Ser Gly Ala Leu Thr Ser
            165             170             175

Gly Val His Thr Phe Pro Ala Val Leu Gln Ser Ser Gly Leu Tyr Ser
            180             185             190

Leu Ser Ser Val Val Thr Val Pro Ser Ser Ser Leu Gly Thr Lys Thr
        195             200             205

Tyr Thr Cys Asn Val Asp His Lys Pro Ser Asn Thr Lys Val Asp Lys
        210             215             220

Arg Val Glu Ser Lys Tyr Gly Pro Pro Cys Pro Ser Cys Pro Ala Pro
225             230             235             240

Glu Phe Leu Gly Gly Pro Ser Val Phe Leu Phe Pro Pro Lys Pro Lys
            245             250             255

Asp Thr Leu Met Ile Ser Arg Thr Pro Glu Val Thr Cys Val Val Val
            260             265             270

Asp Val Ser Gln Glu Asp Pro Glu Val Gln Phe Asn Trp Tyr Val Asp
        275             280             285

Gly Val Glu Val His Asn Ala Lys Thr Lys Pro Arg Glu Glu Gln Phe
        290             295             300

Asn Ser Thr Tyr Arg Val Val Ser Val Leu Thr Val Leu His Gln Asp
305             310             315             320

Trp Leu Asn Gly Lys Glu Tyr Lys Cys Lys Val Ser Asn Lys Gly Leu
            325             330             335

Pro Ser Ser Ile Glu Lys Thr Ile Ser Lys Ala Lys Gly Gln Pro Arg
            340             345             350

Glu Pro Gln Val Tyr Thr Leu Pro Pro Ser Gln Glu Glu Met Thr Lys
        355             360             365

Asn Gln Val Ser Leu Thr Cys Leu Val Lys Gly Phe Tyr Pro Ser Asp
        370             375             380

Ile Ala Val Glu Trp Glu Ser Asn Gly Gln Pro Glu Asn Asn Tyr Lys
385             390             395             400

Thr Thr Pro Pro Val Leu Asp Ser Asp Gly Ser Phe Phe Leu Tyr Ser
            405             410             415

Arg Leu Thr Val Asp Lys Ser Arg Trp Gln Gln Gly Asn Val Phe Ser
            420             425             430

Cys Ser Val Met His Glu Ala Leu His Asn His Tyr Thr Gln Lys Ser
        435             440             445

Leu Ser Leu Ser Leu Gly Lys
450             455
```

HIGH AFFINITY HUMAN ANTIBODIES TO HUMAN IL-18 RECEPTOR

CROSS-REFERENCE TO RELATED APPLICATIONS

This application claims the benefit under 35 USC § 119(e) of U.S. Provisional 60/790,081 filed 7 Apr. 2006, which application is herein specifically incorporated by reference in its entirety.

FIELD OF THE INVENTION

The present invention related to human antibodies and antibody fragments specific for human interleukin 18 receptor alpha (hIL-18Rα) (SEQ ID NO:1), pharmaceutical compositions, and therapeutic methods thereof.

STATEMENT OF RELATED ART

Two interleukin-18 receptors are known, IL-18Rα and IL-18Rβ. IL-18Rα is also known as 2F1, interleukin-1 receptor related protein 1 (IL-1Rrp1), IL-18R1, IL-1R5, IL-1Rrp and IL-1 receptor-like (Parnet et al. U.S. Pat. No. 5,776,731; U.S. Pat. No. 6,090,918; Sims et al. U.S. Pat. No. 6,589,764. U.S. Pat. No. 6,600,022 (Torigoe et al.) discloses a murine monoclonal antibody specific to IL-18Rα comprising variable heavy and light chain protein sequences.

Methods to produce antibodies useful as human therapeutics include generation of chimeric antibodies and humanized antibodies (see, for example, U.S. Pat. No. 6,949,245). WO 94/02602 (Abgenix) (herein specifically incorporated by reference) describes a method of generating nonhuman transgenic mice capable of producing human antibodies.

BRIEF SUMMARY OF THE INVENTION

In a first aspect, the invention provides an agent, preferably a recombinant human antibody, that specifically binds human interleukin-18 receptor alpha (hIL-18Rα) (SEQ ID NO:1). The binding agents of the invention are characterized by binding to hIL-18Rα with high affinity and by the ability to neutralize hIL-18 activity, including IL-18-induced interferon gamma expression and IL-18-induced cellular activation. The agents can be antibodies that are full-length (for example, an IgG1, IgG2, IgG4, IgG4 mutants, etc.) or may comprise an antigen-binding portion or antibody fragment (for example, a Fab, F(ab')$_2$ or scFv fragment), and may be modified to effect functionality, e.g., to eliminate residual effector functions (Glu which eliminates residual effector functions (Reddy et al. (2000) J. Immunol. 164:1925-1933).

In one embodiment, an agent capable of specifically binding hIL-18Rα comprises a light chain variable region (LCVR) selected from the group consisting of SEQ ID NO: 5, 9, 13, 17, 21, 25, 29, 33, 37, 41, 45, 49, 53, 57, 61, 65, 69, 73, 77, and 81, or a substantially identical fragment or sequence modified by an amino acid substitution, deletion or addition thereof.

In one embodiment, an agent capable of specifically binding hIL-18Rα comprises a heavy chain variable region (HCVR) selected from the group consisting of SEQ ID NO: 3, 7, 11, 15, 19, 23, 27, 31, 35, 39, 43, 47, 51, 55, 59, 63, 67, 71, 75, and 79, or a substantially identical fragment or sequence modified by an amino acid substitution, deletion or addition thereof.

In one embodiment, an agent capable of specifically binding hIL-18Rα comprises a LCVR encoded by a nucleic acid sequence selected from the group consisting of SEQ ID NO: 4, 8, 12, 16, 20, 24, 28, 32, 36, 40, 44, 48, 52, 56, 60, 64, 68, 72, 76, and 80, or a substantially identical fragment or sequence modified by an amino acid substitution, deletion or addition thereof.

In one embodiment, an agent capable of specifically binding hIL-18Rα comprises a HCVR encoded by a nucleic acid sequence selected from the group consisting of SEQ ID NO: 2, 6, 10, 14, 18, 22, 26, 30, 34, 38, 42, 46, 50, 54, 58, 62, 66, 70, 74, and 78, or a substantially identical fragment or sequence modified by an amino acid substitution, deletion or addition thereof.

In another embodiment, an hIL-18Rα-binding agent comprises SEQ ID NO:3 and 5; 7 and 9; 11 and 13; 15 and 17; 19 and 21; 23 and 25; 27 and 29; 31 and 33; 35 and 37; or 29 and 41. Encompassed by the invention are modifications to remove undesirable glycosylation sites, for example substitution of N92 of SEQ ID NO:5 (VH1F9) to another amino acid, such as D or E.

In an aspect of the invention, an agent capable of specifically binding hIL-18Rα is provided, comprising a light chain CDR3 domain selected from the group consisting of about amino acids 89-96 of SEQ ID NO:5; about 89-97 of SEQ ID NO:9 or 37; about 96-103 of SEQ ID NO:13; about 95-103 of SEQ ID NO:17, 21, 25, 29, or 41; and about 95-102 of SEQ ID NO:33, or a substantially identical sequence modified by an amino acid substitution, deletion or addition thereof. In a further embodiment, the agent further comprises a light chain CDR1 domain selected from the group consisting of amino acids about 27-32 of SEQ ID NO:5, 9, or 37; and about 27-38 of SEQ ID NO:13, 17, 21, 25, 29, 33, or 41; or a substantially identical sequence modified by an amino acid substitution, deletion or addition thereof. In a further embodiment, the agent further comprises a light chain CDR2 domain selected from the group consisting of amino acids about 50-52 of SEQ ID NO:5, 9, or 37; and about 56-58 of SEQ ID NO:13, 17, 21, 25, 29, 33, or 41; or a substantially identical sequence modified by an amino acid substitution, deletion or addition thereof.

In an aspect of the invention, an agent capable of specifically binding hIL-18Rα is provided, comprising a heavy chain CDR3 domain selected from the group consisting of amino acids about 97-110 of SEQ ID NO:3; about 97-117 of SEQ ID NO:7; about 97-104 of SEQ ID NO:11, 15, 19, 23, 27, 39; about 97-107 of SEQ ID NO:31, and about 100-108 of SEQ ID NO:35, or a substantially identical sequence modified by an amino acid substitution, deletion or addition thereof. In a further aspect, the agent further comprises a heavy chain CDR1 domain selected from the group consisting of amino acids about 26-33 of SEQ ID NO:3, 7, 11, 15, 19, 23, 27, 31, or 39; and about 26-35 of SEQ ID NO:35; or a substantially identical sequence modified by an amino acid substitution, deletion or addition thereof. In a further embodiment, the agent further comprises a heavy chain CDR2 domain selected from the group consisting of amino acids about 51-58 of SEQ ID NO:3, 7, 11, 15, 19, 23, 27, 31, or 39; and about 53-61 of SEQ ID NO:35, or a substantially identical sequence modified by an amino acid substitution, deletion or addition thereof.

In an aspect of the invention, an agent capable of specifically binding hIL-18Rα is provided, comprising a light chain CDR3 domain selected from the group consisting of amino acids about 89-96 of SEQ ID NO:5; about 89-97 of SEQ ID NO:9 or 37; about 96-103 of SEQ ID NO:13, about 95-103 of SEQ ID NO:17, 21, 25, 29, or 41; and about 95-102 of SEQ ID NO:33; and a heavy chain CDR3 domain selected from the group consisting of amino acids about 97-110 of SEQ ID NO:3; about 97-117 of SEQ ID NO:7; about 97-104 of SEQ ID NO:11, 15, 19, 23, 27, or 39, about 97-107 of SEQ ID NO:31; and about 100-108 of SEQ ID NO:35; or a substantially identical sequence modified by an amino acid substitution, deletion or addition thereof.

In an aspect of the invention, an agent capable of specifically binding hIL-18Rα is provided, comprising a light chain CDR1 domain selected from the group consisting of amino acids about 27-32 of SEQ ID NO:5, 9, or 37; and about 27-38 of SEQ ID NO:13, 17, 21, 25, 29, 33, or 41; a light chain CDR2 domain selected from the group consisting of amino acids about 50-52 of SEQ ID NO:5, 9, or 37; and about 56-58 of SEQ ID NO:13, 17, 21, 25, 29, 33, or 41; a light chain CDR3 domain selected from the group consisting of amino acids about 89-96 of SEQ ID NO:5; about 89-97 of SEQ ID NO:9 or 37; about 96-103 of SEQ ID NO:13; about 95-103 of SEQ ID NO:17, 21, 25, 29, or 41; and about 95-102 Of SEQ ID NO:33; a heavy chain CDR1 domain selected from the group consisting of amino acids about 26-33 of SEQ ID NO:3, 7, 11, 15, 19, 23, 27, 31, or 39; and about 26-35 of SEQ ID NO:35; a heavy chain CDR2 domain selected from the group consisting of amino acids about 51-58 of SEQ ID NO:3, 7, 11, 15, 19, 23, 27, 31, or 39; and about 53-61 of SEQ ID NO:35; and a heavy chain CDR3 domain selected from the group consisting of amino acids about 97-110 of SEQ ID NO:3; about 97-117 of SEQ ID NO:7, about 97-104 of SEQ ID NO:11, 15, 19, 23, 27, or 39; about 97-107 of SEQ ID NO:31; and about 100-108 of SEQ ID NO:35, or a substantially identical sequence modified by an amino acid substitution, deletion or addition thereof.

In an aspect, the invention features an isolated binding agent that specifically binds hIL-18Rα, comprising at least one complementary determining region (CDR), wherein the CDR is selected from the group consisting of (i) an amino acid sequence of the formula $X^1$-$X^2$-$X^3$-$X^4$-$X^5$-$X^6$-$X^7$-$X^8$-$X^9$-$X^{10}$ (SEQ ID NO:82), wherein $X^1$=Gly or Tyr; $X^2$=Thr, Tyr or Asp, $X^3$=Phe, Thr, Asn or Ser, $X^4$=Thr, Phe or Val, $X^5$=Ser, Asn, Thr or Ile, and $X^6$=Tyr, Ser, Asn, Gly or Thr; $X^7$=Tyr, Phe or absent; $X^8$=Gly, Tyr, Ser or absent; $X^9$=Ala or absent; and $X^{10}$=Ala or absent; (ii) an amino acid sequence of the formula $X^1$-$X^2$-$X^3$-$X^4$-$X^5$-$X^6$-$X^7$-$X^8$-$X^9$ (SEQ ID NO:83) wherein $X^1$=Ile, Thr or Met, $X^2$=Asn, Arg, Ser, Thr or Tyr, $X^3$=Pro, Thr, Ala, Val or Tyr, $X^4$=Asn, Tyr or Arg, $X^5$=Ser or Asn, $X^6$=Gly, $X^7$=Asn, Gly or Trp, $X^8$=Thr or Tyr, and $X^9$=Asn or absent; (iii) an amino acid sequence of the formula $X^1$-$X^2$-$X^3$-$X^4$-$X^5$-$X^6$-$X^7$-$X^8$-$X^9$-$X^{10}$-$X^{11}$-$X^{12}$-$X^{13}$-$X^{14}$-$X^{15}$-$X^{16}$-$X^{17}$-$X^{18}$-$X^{19}$-$X^{20}$-$X^{21}$ (SEQ ID NO:84) wherein $X^1$=Thr, Ala or Val, $X^2$=Thr or Arg, $X^3$=Pro, Asp, Gly or Glu, $X^4$=Gly, Glu, Trp or Met, $X^5$=Asp, Ala, Phe, Tyr, Thr or Gly, $X^6$=Lys, Arg, Phe, Tyr, Asp or Ala, $X^7$=Trp, Ile, Asp, Ala, Phe or Leu, $X^8$=Asn, Val, Ile, Leu, Asp or Phe; $X^9$=Tyr, Val, Leu, Phe, Ile or absent, $X^{10}$=Tyr, Gly or absent, $X^{11}$=Tyr, Gly or absent, $X^{12}$=Phe, Thr or absent, $X^{13}$=Gln, Thr or absent, $X^{14}$=Phe, Pro or absent, $X^{15}$=Tyr, Trp or absent, $X^{16}$=Gly, Tyr or absent, $X^{17}$=Tyr or absent, $X^{18}$=Gly or absent, $X^{19}$=Met or absent, $X^{20}$=Asp or absent, $X^{21}$=Val or absent; (iv) an amino acid sequence of the formula $X^1$-$X^2$-$X^3$-$X^4$-$X^5$-$X^6$-$X^7$-$X^8$-$X^9$-$X^{10}$-$X^{11}$-$X^{12}$ (SEQ ID NO:85) wherein $X^1$=Gln, $X^2$=His, Asp, Ser or Thr, $X^3$=Ile or Val, $X^4$=Ser, Arg, Leu or Phe, $X^5$=Ile, Asn, Tyr or Ser, $X^6$=Trp, Asp, Ser or Tyr, $X^7$=Ser or absent, $X^8$=Asn or absent, $X^9$=Asn or absent, $X^{10}$=Lys or absent; $X^{11}$=Asn, Thr or absent, and $X^{12}$=Tyr or absent; (v) an amino acid sequence of the formula $X^1$-$X^2$-$X^3$ (SEQ ID NO:86), wherein $X^1$=Ser, Ala, Trp or Asp, $X^2$=Ala or Ser, and $X^3$=Ser; and (vi) an amino acid sequence of the formula $X^1$-$X^2$-$X^3$-$X^4$-$X^5$-$X^6$-$X^7$-$X^8$-$X^9$ (SEQ ID NO:87) wherein $X^1$=Gln or Leu, $X^2$=Gln or Tyr, $X^3$=Ala, Asp, Tyr, Phe or Arg=, $X^4$=Asn, Tyr, Arg, Phe or Gly, $X^5$=Ser, Asn, Thr, Arg or Ile, $X^6$=Phe, Tyr, Pro, Thr or Trp, $X^7$=Pro, Tyr, or Trp, $X^8$=Ser, Arg, Thr, Tyr or Pro, and $X^9$=Thr, Ser or absent.

In an aspect, the invention features an agent capable of binding hIL-18Rα with an $IC_{50}$ of less than about 10 nM, or 500 pM, or 100 pM, preferably less than about 50 pM, more preferably less than about 20 pM, even more preferably less than about 10 pM or less than about 5 pM, as measured by ELISA solution affinity assay.

In an aspect, the invention provides an agent that binds hIL-18Rα with a $K_D$ of less than about 20 nM, about 10 nM, about 5 nM, as measured by surface plasmon resonance (BIAcore™) with monomeric hIL-18 Rα, or about 500 pM, 300 pM, 20 pM, 10 pM or less than about 5 pM as determined by surface plasmon resonance with dimeric hIL-18Rα. In a preferred embodiment, the agent binds hIL-18Rα with an $K_D$ of 20 nM or less, as measured by surface plasmon resonance with monomeric hIL-18Rα and exhibiting reduced cellular cytotoxicity, comprising a heavy chain selected from SEQ ID NO:88, a SEQ ID NO:88 variant with S229P, SEQ ID NO:89, a SEQ ID NO:89 variant with S223P, SEQ ID NO:90, a SEQ ID NO:90 variant with S223P, SEQ ID NO:91, and a SEQ ID NO:91 variant with S236P. In a specific embodiment, SEQ ID NO:88-91 or a variant thereof, further comprise a light chain comprising SEQ ID NO:4, 12, 16 or 8, respectively.

In an aspect, the invention features an agent which specifically binds within domain 3 of hIL-18Rα, e.g., from about amino acid 220 to about amino acid 312 of SEQ ID NO:1. The agent of the invention may further comprise a label, drug or toxin, or be modified with the addition of molecules such as chains of polyethylene glycol.

In an aspect, the invention provides nucleic acid molecules encoding an agent of the invention. Recombinant expression vectors carrying the agent encoding nucleic acids of the invention, and host cells into which such vectors have been introduced, are also encompassed by the invention, as are methods of making the agents of the invention by culturing the host cells of the invention.

In an aspect of the invention, an agent capable of specifically binding hIL-18Rα is provided, comprising a heavy chain CDR3 domain encoded by a nucleic acid sequence selected from the group consisting of nucleotides from about 289 to about 329 of SEQ ID NO:2, about 289 to about 351 of SEQ ID NO:6; about 289 to about 312 of SEQ ID NO:10, 14, 20, 26 and 38; about 289 to about 310 of SEQ ID NO:18, about 289 to 321 of SEQ ID NO:30; and about 298 to about 324 of SEQ ID NO:34, or a sequence modified by a nucleotide substitution, deletion or addition thereof. In a further aspect, the agent further comprises a heavy chain CDR1 domain encoded by a nucleic acid sequence selected from the group consisting of nucleotides from about 76 to about 99 of SEQ ID NO:2, 6, 10, 14, 22, 26, 30 or 38; about 76 to about 98 of SEQ ID NO:18; and about 76 to about 102 of SEQ ID NO:34, or a sequence modified by a nucleotide substitution, deletion or addition thereof. In a further embodiment, the agent further comprises a heavy chain CDR2 domain encoded by a nucleic acid sequence selected from the group consisting of nucleotides from about 151 to about 174 of SEQ ID NO:2, 6, 10, 14, 18, 20, 26, 30 or 38; and about 157 to about 183 of SEQ ID NO:34, or a sequence modified by a nucleotide substitution, deletion or addition thereof.

In an aspect of the invention, an agent capable of specifically binding hIL-18Rα is provided, comprising a light chain CDR3 domain encoded by a nucleic acid sequence selected from the group consisting of nucleotides from about 265 to about 288 of SEQ ID NO:4, about 265 to about 291 of SEQ ID NO:8 and 36; about 283 to about 309 of SEQ ID NO:12, 16, 20, 24, 28 or 40; about 283 to about 306 of SEQ ID NO:32, or a sequence modified by a nucleotide substitution, deletion or addition thereof. In a further aspect, the agent further comprises a light chain CDR1 domain encoded by a nucleic acid sequence selected from the group consisting of nucleotides from about 76 to about 96 of SEQ ID NO:4, 8 and 36; about 79 to about 114 of SEQ ID NO:12, 16, 24, 28, 32 or 40; and about 25 to about 60 of SEQ ID NO:20, or a sequence modified by a nucleotide substitution, deletion or addition thereof. In a further embodiment, the agent further comprises a light chain CDR2 domain encoded by a nucleic acid sequence selected from the group consisting of nucleotides from about 148 to about 156 of SEQ ID NO:4, 8 or 36; and about 166 to about 174 of SEQ ID NO:12, 16, 20, 24, 28, 32 or 40, or a sequence modified by a nucleic acid substitution, deletion or addition thereof.

In one aspect, the invention features a transgenic mouse comprising a human sequence encoding a LCVR or HCVR selected from the group consisting of SEQ ID NO:5, 9, 13, 17, 21, 25, 29, 33, 37, or 41, and SEQ ID NO:3, 7, 11, 15, 19, 23, 27, 31, 35 or 39. In another aspect, the transgenic mouse of the invention comprises a sequence encoding a light chain CDR3 domain selected from the group consisting of amino acids about 89-96 of SEQ ID NO:5; about 89-97 of SEQ ID NO:9 or 37; about 96-103 of SEQ ID NO: 13, about 95-103 of SEQ ID NO:17, 21, 25, 29, or 41; and about 95-102 of SEQ ID NO:33; and a heavy chain CDR3 domain selected from the group consisting of amino acids about 97-110 of SEQ ID NO:3; about 97-117 of SEQ ID NO:7; about 97-104 of SEQ ID NO:11, 15, 19, 23, 27, or 39, about 97-107 of SEQ ID NO:31; and about 100-108 of SEQ ID NO:35.

In one aspect, the invention features a pharmaceutical composition comprising an agent which specifically binds hIL-18Rα and an acceptable carrier.

In one aspect, the invention features methods for inhibiting hIL-18 activity comprising administering a therapeutically effective amount of an agent capable of specifically binding hIL-18Rα. In one embodiment, the method comprises contacting hIL-18Rα with an agent of the invention such that hIL-18 activity is inhibited. In another embodiment, the method comprises administering an agent of the invention to a human subject suffering from a disorder in which IL-18 activity is detrimental such that IL-18 activity in the human subject is inhibited. The disorder can be, for example, sepsis, Systemic Inflammatory Response Syndrome (SIRS), including severe sepsis, septic shock, and sepsis related to cardiac dysfunction; liver injury; arthritis, including rheumatoid arthritis; inflammatory bowel diseases, including Crohn's disease and ulcerative colitis; central nervous system injury, including traumatic head injury; heart disease; hypersensitivity disorders, including delayed-type hypersensitivity; tumor metastasis; atherosclerosis; and peripheral vascular diseases.

Other objects and advantages will become apparent from a review of the ensuing detailed description.

DETAILED DESCRIPTION

Before the present methods are described, it is to be understood that this invention is not limited to particular methods, and experimental conditions described, as such methods and conditions may vary. It is also to be understood that the terminology used herein is for the purpose of describing particular embodiments only, and is not intended to be limiting, since the scope of the present invention will be limited only by the appended claims.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference in their entirety.

The term "human IL18Rα" (hIL-18Rα) (SEQ ID NO:1), refers to a human cytokine receptor that exists as a 60 kD membrane-associated form, the biologically active form of which is composed of IL-18 and a dimer of noncovalently bound IL-18Ra and IL-18Racp. The structure of hIL-18Rα is described further in, for example, Azam et al. (2003) J Immunol. 171:6574-80. The term hIL-18Rα is intended to include an extracellular domain of hIL-18Rα, which can be prepared by standard recombinant expression methods or purchased commercially.

The agents of the invention are preferably an antibody or antibody fragment. An "antibody" is intended to refer to immunoglobulin molecules consisting of four polypeptide chains, two heavy (H) chains and two light (L) chains interconnected by disulfide bonds. Each heavy chain has a heavy chain variable region (HCVR or VH) and a heavy chain constant region. The heavy chain constant region contains three domains, CH1, CH2 and CH3. Each light chain has of a light chain variable region and a light chain constant region. The light chain constant region consists of one domain (CL). The VH and VL regions can be further subdivided into regions of hypervariability, termed complementarity determining regions (CDR), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, FR4.

The term "high affinity" antibody refers to those antibodies having a binding affinity to hIL-18Rα of at least $10^{-10}$ M; preferably $10^{-11}$ M; even more preferably $10^{-12}$ M, as measured by surface plasmon resonance (e.g., BIAcore™) or ELISA.

The term "antigen-binding portion" of an antibody (or "antibody fragment"), refers to one or more fragments of an antibody that retain the ability to specifically bind to an antigen (e.g., hIL-18Rα). Examples of binding fragments encompassed within the term "antigen-binding portion" of an antibody include (i) a Fab fragment, a monovalent fragment consisting of the VL, VH, CL and CH1 domains; (ii) a F(ab')$_2$ fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al. (1989) Nature 241:544-546), which consists of a VH domain, (vi) an isolated CDR, and (vii) an scFv, the two domains of the Fv fragment, VL and VH, joined by a synthetic linker to form a single protein chain in which the VL and VH regions pair to form monovalent molecules. Other forms of single chain antibodies, such as diabodies are also encompassed (see e.g., Holliger et al. (1993) PNAS USA 90:6444-6448; Poljak et al. (1994) Structure 2:1121-1123).

Still further, an antibody or antigen-binding portion thereof may be part of a larger immunoadhesion molecule, formed by covalent or noncovalent association of the antibody or antibody portion with one or more other proteins or peptides. Examples of such immunoadhesion molecules include use of the streptavidin core region to make a tetrameric scFv molecule (Kipriyanov et al. (1995) Human Antibodies and Hybridomas 6:93-101) and use of a cysteine residue, a marker peptide and a C-terminal polyhistidine tag to make bivalent and biotinylated scFv molecules (Kipriyanov et al. (1994) Mol. Immunol. 31:1047-1058). Antibody portions, such as Fab and F(ab')$_2$ fragments, can be prepared from whole antibodies using conventional techniques, such as papain or pepsin digestion, respectively, of whole antibodies. Moreover, antibodies, antibody portions and immunoadhesion molecules can be obtained using standard recombinant DNA techniques, as described herein.

The term "human antibody", as used herein, is intended to include antibodies having variable and constant regions derived from human germline immunoglobulin sequences. The human antibodies of the invention may include amino acid residues not encoded by human germline immunoglobulin sequences (e.g., mutations introduced by random or site-specific mutagenesis in vitro or by somatic mutation in vivo), for example in the CDRs and in particular CDR3. However, the term "human antibody", as used herein, is not intended to include antibodies in which CDR sequences derived from the germline of another mammalian species, such as a mouse, have been grafted onto human framework sequences.

The term "recombinant human antibody", as used herein, is intended to include all human antibodies that are prepared, expressed, created or isolated by recombinant means, such as antibodies expressed using a recombinant expression vector transfected into a host cell (described further below), antibodies isolated from a recombinant, combinatorial human antibody library (described further below), antibodies isolated from an animal (e.g., a mouse) that is transgenic for human immunoglobulin genes (see e.g., Taylor et al. (1992) Nucl. Acids Res. 20:6287-6295) or antibodies prepared, expressed, created or isolated by any other means that involves splicing of human immunoglobulin gene sequences to other DNA sequences. Such recombinant human antibodies have variable and constant regions derived from human germline immunoglobulin sequences. In certain embodiments, however, such recombinant human antibodies are subjected to in vitro mutagenesis (or, when an animal transgenic for human Ig sequences is used, in vivo somatic mutagenesis) and thus the amino acid sequences of the VH and VL regions of the recombinant antibodies are sequences that, while derived from and related to human germline VH and VL sequences, may not naturally exist within the human antibody germline repertoire in vivo.

A "neutralizing antibody", as used herein (or an "antibody that neutralized hIL-18 activity"), is intended to refer to an antibody whose binding to hIL-18Rα results in inhibition of the biological activity of hIL-18. This inhibition of the biological activity of hIL-18 can be assessed by measuring one or more indicators of hIL-18 biological activity, such as hIL-18-induced interferon gamma gene expression (either in vitro or in vivo), hIL-18-induced cellular activation and hIL-18 binding to hIL-18Rα. These indicators of hIL-18 biological activity can be assessed by one or more of several standard in vitro or in vivo assays known in the art (see examples below). Preferably, the ability of an antibody to neutralize hIL-18 activity is assessed by inhibition of hIL-18-induced interferon gamma production by KG-1 cells or peripheral blood lymphocytes. As an additional or alternative parameter of hIL-18 activity, the ability of an antibody to inhibit hIL-18-induced expression of a luciferase gene fused to NFKB promoter elements, as a measure of hIL-18-induced cellular activation, can be assessed.

The term "surface plasmon resonance", as used herein, refers to an optical phenomenon that allows for the analysis of real-time biospecific interactions by detection of alterations in protein concentrations within a biosensor matrix, for example using the BIAcore™ system (Pharmacia Biosensor AB, Uppsala, Sweden and Piscataway, N.J.).

The term "$K_D$", as used herein, is intended to refer to the dissociation constant of a particular antibody-antigen interaction.

The term "isolated nucleic acid molecule", as used herein in reference to nucleic acids encoding antibodies or antibody portions (e.g., VH, VL, CDR3) that bind hIL-18Rα is intended to refer to a nucleic acid molecule in which the nucleotide sequences encoding the antibody or antibody portion are free of other nucleotide sequences encoding antibodies or antibody portions that bind antigens other than hIL-18Rα, which other sequences may naturally flank the nucleic acid in human genomic DNA. Thus, for example, an isolated nucleic acid of the invention encoding a VH region of an anti-hIL-18Rα antibody contains no other sequences encoding other VH regions that bind antigens other than hIL-18Rα.

The term "epitope" includes any determinant, preferably a polypeptide determinant, capable of specific binding to an immunoglobulin or T-cell receptor. In certain embodiments, epitope determinants include chemically active surface groupings of molecules such as amino acids, sugars, carbohydrates, phosphoryl groups, or sulfonyl groups, and, in certain embodiments, may have specific three-dimensional structural characteristics, and/or specific charge characteristics. An epitope is a region of an antigen that is bound by an antibody. In certain embodiments, an antibody is said to specifically bind an antigen when it preferentially recognizes its target antigen in a complex mixture of proteins and/or macromolecules.

A protein or polypeptide is "substantially pure," "substantially homogeneous" or "substantially purified" when at least about 60 to 75% of the total protein exhibits a single species of polypeptide. The polypeptide or protein may be monomeric or multimeric. A substantially pure polypeptide or protein will typically comprise about 50%, 60, 70%, 80% or 90% w/w of a protein sample, more usually about 95%, and preferably will be over 99%. Protein purity or homogeneity may be determined by a number of means well known in the art, such as polyacrylamide gel electrophoresis of a protein sample, followed by visualizing a single polypeptide band upon staining the gel with a stain well known in the art. For certain purposes, higher resolution may be provided by using HPLC or other means well known in the art for purification.

The term "polypeptide analog or variant" as used herein refers to a polypeptide that comprises a segment of at least 25 amino acids that has substantial identity to a portion of an amino acid sequence and specifically binds to hIL-18Rα under suitable binding conditions and/or the ability of hIL-18 to bind hIL-18Rα. Typically, polypeptide analogs or variants comprise a conservative amino acid substitution (or insertion or deletion) with respect to the naturally-occurring sequence. Analogs typically are at least 20 amino acids long, preferably at least 50, 60, 70, 80, 90, 100, 150 or 200 amino acids long or longer, and can often be as long as a full-length naturally-occurring polypeptide.

Preferred amino acid substitutions are those which: (1) reduce susceptibility to proteolysis, (2) reduce susceptibility to oxidation, (3) alter binding affinity for forming protein complexes, (4) alter binding affinities, and (4) confer or modify other physicochemical or functional properties of such analogs. Analogs can include various mutations of a sequence other than the naturally-occurring peptide sequence. For example, single or multiple amino acid substitutions (preferably conservative amino acid substitutions) may be made in the naturally-occurring sequence (preferably in the portion of the polypeptide outside the domain(s) forming intermolecular contacts. A conservative amino acid substitution should not substantially change the structural characteristics of the parent sequence (e.g., a replacement amino acid should not tend to break a helix that occurs in the parent sequence, or disrupt other types of secondary structure that characterizes the parent sequence).

Non-peptide analogs are commonly used in the pharmaceutical industry as drugs with properties analogous to those of the template peptide. These types of non-peptide compound are termed "peptide mimetics" or "peptidomimetics" (see, for example, Fauchere (1986) J. Adv. Drug Res. 15:29). Systematic substitution of one or more amino acids of a consensus sequence with a D-amino acid of the same type (e.g., D-lysine in place of L-lysine) may also be used to generate more stable peptides. In addition, constrained peptides comprising a consensus sequence or a substantially identical consensus sequence variation may be generated by methods known in the art (Rizo et al (1992) Ann. Rev. Biochem. 61:387, incorporated herein by reference), for example, by adding internal cysteine residues capable of forming intramolecular disulfide bridges which cyclize the peptide.

The term "percent sequence identity" in the context of nucleic acid sequences refers to the residues in two sequences which are the same when aligned for maximum correspondence. The length of sequence identity comparison may be over a stretch of at least about nine nucleotides or more, usually at least about 18 nucleotides, more usually at least about 24 nucleotides, typically at least about 28 nucleotides, more typically at least about 32 nucleotides, and preferably at least about 36, 48 or more nucleotides. There are a number of different algorithms known in the art which can be used to measure nucleotide sequence identity. For instance, polynucleotide sequences can be compared using FASTA, Gap or Bestfit, which are programs in Wisconsin Package Version 10.0, Genetics Computer Group (GCG), Madison, Wis. FASTA, which includes, e.g., the programs FASTA2 and FASTA3, provides alignments and percent sequence identity of the regions of the best overlap between the query and search sequences (Pearson (1990) Methods Enzymol. 183: 63-98 and (2000) Methods Mol. Biol. 132:185-219, each herein incorporated by reference). Unless otherwise specified, default parameters for a particular program or algorithm are used. For instance, percent sequence identity between nucleic acid sequences can be determined using FASTA with its default parameters (a word size of 6 and the NOPAM factor for the scoring matrix) or using Gap with its default parameters as provided in GCG Version 6.1, herein incorporated by reference.

The term "substantial similarity" or "substantial sequence similarity," when referring to a nucleic acid or fragment thereof, indicates that, when optimally aligned with appropriate nucleotide insertions or deletions with another nucleic acid (or its complementary strand), there is nucleotide sequence identity in at least about 90%, preferably at least about 95%, and more preferably at least about 96%, 97%, 98% or 99% of the nucleotide bases, as measured by any well-known algorithm of sequence identity, such as FASTA, BLAST or GAP, as discussed above.

As applied to polypeptides, the term "substantial identical" means that two peptide sequences, when optimally aligned, such as by the programs GAP or BESTFIT using default gap weights, share at least 80% sequence identity, preferably at least 90% or 95% sequence identity, even more preferably at least 98% or 99% sequence identity. Preferably, residue positions which are not identical differ by conservative amino acid substitutions.

Sequence similarity for polypeptides, which is also referred to as sequence identity, is typically measured using sequence analysis software. Protein analysis software matches similar sequences using measures of similarity assigned to various substitutions, deletions and other modifications, including conservative amino acid substitutions. For instance, GCG contains programs such as "GAP" and "BESTFIT" which can be used with default parameters to determine sequence homology or sequence identity between closely related polypeptides, such as homologous polypeptides from different species of organisms or between a wild type protein and a mutant thereof. See, e.g., GCG Version 6.1. Polypeptide sequences also can be compared using FASTA using default or recommended parameters, a program in GCG Version 6.1. FASTA (e.g., FASTA2 and FASTA3) provides alignments and percent sequence identity of the regions of the best overlap between the query and search sequences (Pearson (2000) supra). Another preferred algorithm when comparing a sequence of the invention to a database containing a large number of sequences from different organisms is the computer program BLAST. See, e.g., Altschul et al. (1990) J. Mol. Biol. 215: 403).

Preparation of Human Antibodies

Methods for generating human antibodies include, for example, VelocImmune® (Regeneron Pharmaceuticals), XenoMouse™ technology (Abgenix), the "minilocus" approach, and phage display. The VelocImmune® technology (U.S. Pat. No. 6,596,541) encompasses a method of generating a high specificity fully human antibody to a select antigen. This technology involves generation of a transgenic mouse having a genome comprising human heavy and light chain variable regions operably linked to endogenous mouse constant region loci such that the mouse produces an antibody comprising a human variable region and a mouse constant region in response to antigenic stimulation. The DNA encoding the variable regions of the heavy and light chains of the antibody are isolated and operably linked to DNA encoding the human heavy and light chain constant regions. The DNA is then expressed in a cell capable of expressing the fully human antibody. In specific embodiment, the cell is a CHO cell.

The XenoMouse™ technology (Green et al. (1994) Nature Genetics 7:13-21) generates a mouse having both human variable and constant regions from the heavy chain and kappa light chain loci. In an alternative approach, others have utilized a "minilocus" approach in which an exogenous Ig locus is mimicked through inclusion of individual genes from the Ig locus (see, for example, U.S. Pat. No. 5,545,807). The DNA encoding the variable regions can be isolated with or without being operably linked to the DNA encoding the human heavy and light chain constant region. Other methods of generating human antibodies, including isolation from a human donor, are known. See, for example, U.S. Pat. No. 6,787,637 (herein specifically incorporated by reference in its entirety).

Antibodies may be therapeutically useful in blocking a ligand-receptor interaction or inhibiting receptor component interaction, rather than by killing cells through fixation of complement and participation in complement dependent cytotoxicity (CDC). The constant region of an antibody is important in the ability of an antibody to fix complement and participate in CDC. Thus, the isotype of an antibody may be selected on the basis of whether it is desirable for the antibody to fix complement. Generally, in the present case, it is not required for the antibodies of the invention to fix complement and participate in CDC, and thus desirable isotypes include human IgG2 and IgG4.

Human immunoglobulins can exist in two forms that are associated with hinge heterogeneity. In one form, an immunoglobulin molecule comprises a stable four chain construct of approximately 150-160 kDa in which the dimers are held together by an interchain heavy chain disulfide bond. In a second form, the dimers are not linked via interchain disulfide bonds and a molecule of about 75-80 kDa is formed composed of a single light and heavy chain. These forms have been extremely difficult to separate, even after affinity purification.

The frequency of appearance of the second form in various intact IgG isotypes is due to, but not limited to, structural differences associated with the hinge region isotype of the antibody. In fact, a single amino acid substitution in the hinge region of the human IgG4 hinge can significantly reduce the appearance of the second form (Angal et al. 1993. Molecular Immunology 30: 105) to levels typically observed using a human IgG1 hinge. The instant invention encompasses antibodies having one or more mutations in the hinge, CH2 or CH3 region, which may be desirable, for example, in production to improve the yield of the desired antibody form.

Antibodies of the invention are prepared with the use of VelocImmune® technology. A transgenic mouse in which the endogenous immunoglobulin heavy and light chain variable regions are replaced with the corresponding human variable regions is challenged with the antigen of interest, and lymphatic cells (such as B-cells) recovered from the mice that express antibodies. The lymphatic cells may be fused with a myeloid-type cell line to prepare immortal hybridoma cell lines, and such hybridoma cell lines are screened and selected to identify hybridoma cell lines that produce antibodies specific to the antigen of interest. DNA encoding the variable regions of the heavy chain and light chain may be isolated and linked to desirable isotypic constant regions of the heavy chain and light chain. Such an antibody protein may be produced in a cell, such as a CHO cell. Alternatively, DNA encoding the antigen-specific chimeric antibodies may be isolated directly from antigen-specific lymphocytes.

In one embodiment, the transgenic mouse comprises up to 12 functional human variable heavy chain genes and up to 11 functional human variable kappa light chain genes (MI). In another embodiment, the transgenic mouse comprises from 25 to 30 human variable heavy chain genes and from 18 to 20 human variable kappa light chain genes (MII). In yet another embodiment, the transgenic mouse comprises from 43 to 48 human variable heavy chain genes and from 20 to 22 human variable kappa light chain genes (MIII). In yet another embodiment, the transgenic mouse comprises about 80 human variable heavy chain genes and about 40 human variable kappa light chain genes (MVIII).

In general, the antibodies of the instant invention possess very high affinities, typically possessing KDS of from about $10^{-9}$ through about $10^{-11}$ M, when measured by binding to antigen either immobilized on solid phase or in solution phase.

Epitope Mapping and Related Technologies

To screen for antibodies which bind to a particular epitope (e.g., those which block binding of IgE to its high affinity receptor), a routine cross-blocking assay such as that described in Harlow and Lane, Antibodies (1990) Cold Spring Harbor Laboratory Press, can be performed. Other methods include alanine scanning mutants, peptide blots (Reineke (2004) Methods Mol Biol 248:443-63) (herein specifically incorporated by reference in its entirety), or peptide cleavage analysis. In addition, methods such as epitope excision, epitope extraction and chemical modification of antigens can be employed (Tomer (2000) Protein Science: 9: 487-496, herein specifically incorporated by reference in its entirety).

The term "epitope" refers to a site on an antigen to which B and/or T cells respond. B-cell epitopes can be formed both from contiguous amino acids or noncontiguous amino acids juxtaposed by tertiary folding of a protein. Epitopes formed from contiguous amino acids are typically retained on exposure to denaturing solvents, whereas epitopes formed by tertiary folding are typically lost on treatment with denaturing solvents. An epitope typically includes at least 3, and more usually, at least 5 or 8-10 amino acids in a unique spatial conformation. Antibodies that recognize the same epitope can be verified in a simple immunoassay showing the ability of one antibody to block the binding of another antibody to a target antigen.

Functional Analysis

Modification-Assisted Profiling (MAP), also known as Antigen Structure-based Antibody Profiling (ASAP) is a method that categorizes large numbers of monoclonal antibodies (mAbs) directed against the same antigen according to the similarities of the binding profile of each antibody to chemically or enzymatically modified antigen surfaces (US Patent Publication No. 2004/0101920, herein specifically incorporated by reference in its entirety). Each category may reflect a unique epitope either distinctly different from or partially overlapping with epitope represented by another category. This technology allows rapid filtering of genetically identical antibodies, such that characterization can be focused on genetically distinct antibodies. When applied to hybridoma screening, MAP may facilitate identification of rare hybridoma clones that produce mAbs having the desired characteristics. MAP may be used to sort the hIL-18Rα antibodies of the invention into groups of antibodies binding different epitopes.

The antigen protein may be immobilized on either biosensor chip surfaces or polystyrene beads. The latter can be processed with, for example, an assay such as multiplex Luminex™ detection assay (Luminex Corp., Austin, Tex.). Because of the capacity of Luminex™ to handle multiplex analysis with up to 100 different types of beads, Luminex™ provides almost unlimited antigen surfaces with various modifications, resulting in improved resolution in antibody epitope profiling over a biosensor assay.

EXAMPLES

The following example is put forth so as to provide those of ordinary skill in the art with a complete disclosure and description of how to make and use the methods and compositions of the invention, and are not intended to limit the scope of what the inventors regard as their invention. Efforts have been made to ensure accuracy with respect to numbers used (e.g., amounts, temperature, etc.) but some experimental errors and deviations should be accounted for. Unless indicated otherwise, parts are parts by weight, molecular weight is average molecular weight, temperature is in degrees Centigrade, and pressure is at or near atmospheric.

Example 1

Generation of Human Antibodies to Human IL-18Rα

Immunization of rodents can be done by any methods known in the art (see, for example, Harlow and Lane, Antibodies (supra); Malik and Lillehoj, Antibody techniques: Academic Press, 1994, San Diego). In a preferred embodiment, antigen is administered directly to mice which comprise DNA loci encoding both human Ig heavy chain variable region and kappa light chain variable region (VelocImmune®), with an adjuvant to stimulate the immune response. Such an adjuvant includes complete and incomplete Freund's adjuvant, MPL+TDM adjuvant system (Sigma), or RIBI (muramyl dipeptides) (see O'Hagan (2000) Vaccine Adjuvant, Humana Press, Totawa, N.J.). Such an adjuvant can prevent rapid dispersal of polypeptide by sequestering the antigen in a local depot, and may contain factors that can stimulate host immune response. In another preferred embodiment, the antigen is administered indirectly as DNA plasmid that contains an hIL-18Rα gene and expresses hIL-18Rα using the host cellular protein expression machinery to produce antigen in vivo. In both approaches, the immunization schedule requires several administrations spaced by a few weeks. The antibody immune response is monitored by standard antigen specific immunoassay. When animals reached their maximum immune response, the antibody expressing B cells were harvested and fused with mouse myeloma cells to preserve their viability, forming hybridoma cells. To select functionally desirable antibody expressing cells, conditioned medium of the cells was screened against their antigen specificity as well as preferred epitope or functionality by hIL-18Rα binding affinity and preferred epitope of blocking hIL-18 binding to hIL-18Rα by surface plasmon resonance (BIAcore®) and immunoassays, and in vitro IL-18 neutralization efficacy, as described below.

Antibodies were generated as described above, 10 of which are shown in amino acid sequences SEQ ID NO:5, 9, 13, 17, 21, 25, 29, 33, 37, 41, 45, 49, 53, 57, 61, 65, 69, 73, 77, and 81 (LCVR) and SEQ ID NO: 3, 7, 11, 15, 19, 23, 27, 31, 35, 39, 43, 47, 51, 55, 59, 63, 67, 71, 75,and 79, (HCVR).

Example 2

Affinity Binding and Blocking Determinations

The $K_D$ of the antigen binding to the selected antibodies described above were determined by surface kinetics on a real-time biosensor surface plasmon resonance assay (BIAcore™). The antibody derived from hybridoma was captured on an anti-mouse IgG surface and exposed to various concentrations of hIL-18Rα-hFc fusion protein. Kinetic analysis using evaluation software was performed to obtain the association and dissociation rate constants. Results are shown in Table 1.

Binding affinity of the antibodies to antigen were also measured using a immunoassay. Antibodies were characterize from hybridoma conditioned medium or as purified protein. Protein was purified after hybridoma cells were grown in low IgG medium and affinity purified using Protein G. $IC_{50}$ of antigen binding was determined with an ELISA-based assay. Briefly, constant amounts of antibody at different levels, either in hybridoma conditioned medium or purified, were premixed with serial dilutions of antigen protein, hIL-18Rα-hFc, ranging from 0 to 10 mg/ml, and incubated for two hours at room temperature to reach pseudo-binding equilibrium between the antibody and antigen. These solutions were then transferred to 96-well hIL-18Rα-hFc pre-coated plates (solid phase) to allow the free-antibody in the mixtures to bind to plate-coated hIL-18Rα-hFc. The plates were typically coated with 1 to 2 μg/ml hIL-18Rα-hFc protein in PBS solution overnight at 4° C. followed by BSA nonspecific blocking. After washing off excess antibody in solution, the plate-bound antibodies were detected with an HRP-conjugated goat anti-mouse IgG polyclonal antibody reagent and developed using either colorimetric or chemiluminescent substrates. The dependency of the signals on the concentrations of antigen in solution was analyzed with a 4 parameter fit analysis using Prism™ software from Graph Pad™ and reported as $IC_{50}$ that render 50% reduction of antibody binding to plate-coated antigen. Results are showed in Table 1 (*conditioned medium).

TABLE 1

Antigen Binding Affinity

| Antibody | ELISA $IC_{50}$ nM | BIAcore ™ $K_D$ nM* |
|---|---|---|
| VK8E1 | 0.017 | 0.01 |
| VK5G1 | 0.002 | 0.052 |
| VK2C2 | 0.007 | 0.003 |
| VK3H5 | 0.007 | 0.002 |
| VJ7D5 | 0.003 | 0.005 |
| VK2E5 | 0.010 | 0.001 |
| VI2H10 | 1.7 | 0.495 |
| VH1F9 | 0.026 | 0.135 |
| VI2C4-11 | 0.009 | 0.054 |
| VI2C4-18 | 0.019 | 0.079 |
| VI2A5 | 0.011 | 0.002 |

Conversion of hybridoma-derived chimeric IgG of human variable and mouse constant regions in both heavy and light chains to fully human IgG did not affect antigen binding. Both mouse IgG1 and human IgG4 versions of the derived antibody were measured to determine $K_D$ for monomeric antigen using BIAcore™ (Table 2). Binding affinity of monomeric receptor was measured by capturing mAb from subclone hybridoma supernatant and CHO conditioned media over amine coupled anti-mouse IgG and anti-human IgG. Varying concentrations of 50 nM-12.5 nM of monomeric receptor, hIL18Rα-hIL-18Rb-myc-myc-his, were injected over the captured surface. Data were processed and analyzed using a 1:1 binding model and $K_D$ values were calculated.

TABLE 2

Chimeric Mouse IgG and Fully Human IgG Binding to Monomeric Antigen

| Ab | Isotype | $K_D$ (nM) |
|---|---|---|
| VH1F9-18 | human IgG4 | 6.00 |
| VH1F9-18 | mouse IgG1 | 6.81 |
| VK5G1-15 | human IgG4 | 4.80 |
| VK5G1-15 | mouse IgG1 | 4.68 |
| VK-2C2-22 | human IgG4 | 2.16 |
| VK-2C2-22 | mouse IgG1 | 2.18 |
| VI-2H10-7 | human IgG4 | 19.20 |
| VI-2H10-7 | mouse IgG1 | 17.00 |

The ability of the test antibody to block (inhibit) hIL-18 binding to the IL-18Rα receptor was determined using surface plasmon resonance. Purified antigen IL-18R1-hFc molecules were captured by goat anti-human IgG polyclonal antibodies that were immobilized on a CM-5 surface through amine coupling chemistry, to a density of 250 RU. An IL-18 solution, 0.25 ml at 50 nM, was then injected over the receptor surface and the bound IL-18 was recorded (first injection of hIL-18). The bound hIL-18 was then removed with a pulse of 3 M $MgCl_2$ following by conditioning buffer. Anti-hIL18R1 antibody in hybridoma-conditioned medium was then injected over the captured receptor surface followed by a second injection of hIL-18. The percent reduction in hIL-18 binding resulting from preformed antibody and receptor complex was used as a score to define IL-18 blockers (antagonists) from non-blockers. Results are shown in Table 3 (* conditioned medium).

TABLE 3

Identification of IL-18 Blockers

| Antibody | % Blocking* |
|---|---|
| VK8E1 | 96 |
| VK5G1 | 92 |
| VK2C2 | 98 |
| VK3H5 | 96 |
| VJ7D5 | 91 |
| VK2E5 | 98 |
| VI2H10 | 82 |
| VH1F9 | 96 |
| VI2C4-11 | 41 |
| VI2C4-18 | 41 |
| VI2A5 | 0 |

Example 3

In Vitro Neutralization of hIL-18 Activity

An HEK293/NFkB-luciferase bioassay was used to determine the ability of the hIL-18Rα-specific antibodies of the invention to block the activity of hIL-18. Human embryonic kidney 293 cells (HEK293) were transfected with an NFκB-luciferase reporter plasmid. By placing an NFκB promoter element upstream of the luciferase gene one can monitor NFκB activity in cells. When cells containing the HEK293/NFκB luciferase construct and the IL-18 receptors were stimulated with hIL-18, the luciferase gene was expressed and luciferase activity detected in cell lysates. A stable transfected cell line, HEK293/D9, was first selected for good response to IL-1β as detected by luciferase activity and then transfected with the hIL-18Rα (IL-IRrp) and IL-18Rβ (IL1RAcPL) receptors to produce hIL-18-NFκB-luciferase cells.

For the assay, hIL-18-NFκB-luciferase cells were suspended at $1.25 \times 10^5$ cells per ml in medium and 0.08 ml of cells plated at 10,000 cells per well in a 96-well tissue culture plate. Plates were incubated for ~16 hours at 37° C. in a humidified 5% $CO_2$ incubator. Hybridoma supernatants were quantified by an antigen-specific ELISA. 0.05 ml of serial dilutions, 0-10 nM, of the hIL-18Ralpha antibodies were added to the 96-well plate containing the hIL-18-NFκB-luciferase cells. After a 1 hour incubation, 2 pM of recombinant human IL-18 was added. Control wells contained no hIL-18Rα-specific antibodies. After incubation at 37° C. for 6 hours in a humidified 5% $CO_2$ incubator, the plates were equilibrated to room temperature for ~30 minutes and 130 µl of Steady-Glo™ luciferase substrate (Promega) was added. Luminescence intensity was measured using a multilabel counter, $IC_{50}$, which is a 50% reduction in hIL-18 stimulated activity, were determined with a 4 parameter fit analysis using Prism™ software from Graph Pad™. Table 4 shows the bioassay IC50 values of the IL-18Rα hybridoma supernatants (Prot G purified protein).

KG-1 bioassay. The KG-1 bioassay is an endogenous bioassay used to determine blocking of IL-18 signaling. KG-1 cells are a myelogenous leukemia-derived cell line with endogenous IL18Rα and β receptors that when stimulated with the addition of IL-18, produce IFNγ. For the assay KG-1 cells were washed twice with media and suspended at $6 \times 10^5$ cells per ml in medium and 30,000 cells per well were plated in a 96-well tissue culture plate. Plates were incubated for ~24 hours at 37° C. in a humidified 5% $CO_2$ incubator. rhTNFa was added to 40 ng/ml as a co-stimulator along with 0.05 ml of serial dilutions, 0-12.5 nM, of the hIL-18Rα-specific antibodies and plates were incubated for 1 hour 37° C. in a humidified 5% $CO_2$ incubator. 0.025 ml of hIL-18 was added to the wells at a final concentration of 90 pM and the well volume was adjusted to 0.2 ml with media. Control wells contained no hIL-18Rα-specific antibody. Cells were incubated for 24 hours 37° C. in a humidified 5% $CO_2$ incubator. Media from the wells was analyzed to determine the amount of interferon gamma production using an OptE1A ELISA (BD cat #555142).

Standard curves were generated by linear regression of standards using GraphPad Prism™ to determine X from Y to get pg/ml values for cell supernatants by OD. Values of interferon gamma were analyzed vs Log M concentrations of antibody by non-linear regression analysis sigmoidal dose response to give an IC50 value for antibody inhibition of hIL-18 bioactivity. Table 4 shows the bioassay $IC_{50}$ values of the IL-18Rα hybridoma supernatants (Prot G purified protein).

TABLE 4

In Vitro Luciferase and KG-1 Bioassays

| Antibody | Luciferase Bioassay (IC50 nM) | KG-1 Bioassay (IC50 nM) |
|---|---|---|
| VK8E1 | 0.331 | 0.025 |
| VK5G1 | 0.166 | 0.028 |
| VK2C2 | 0.139 | 0.031 |
| VK3H5 | 0.134 | 0.040 |
| VJ7D5 | 0.194 | 0.064 |
| VK2E5 | 0.336 | 0.047 |
| VI2H10 | 0.196 | 0.064 |
| VH1F9 | 0.653 | 0.085 |
| VI2C4-11 | 1.06 | 0.125 |
| VI2C4-18 | 0.722 | 0.132 |
| VI2A5 | 2.58 | 0.21 |

Example 4

Epitope Mapping Analysis

Preliminary studies using monoclonal antibodies raised against hIL-18Rα (Swiss-Prot entry Q13478) have shown that these antibodies inhibit the binding of hIL-18 to the receptor. Use of a variety of in vitro protease digestions of the recombinant hIL-18 receptor ecto-domain fused to murine Fc has revealed the binding epitope of these monoclonals to be contained near or within the third immunoglobulin domain (residues 220-312 as defined by Swiss-Prot) of the hIL-18 receptor extracellular domain.

Using Ficin protease digestion, 4 Coomassie stained bands were identified for both non-reduced (200, 140, 55 and 42 kD) digests and reduced (95, 60, 42 and 30 kD) digests. Comparing the data obtained from analysis of the 60 kD vs 42 kD reduced bands using a combination of immunodetection and N-terminal protein sequencing, a 60 kD band was observed which possessed immunoreactivity towards the anti-IL18R1 antibodies, while the 42 kD band revealed loss of anti-IL18 receptor ecto-domain immunoreactivity. Since the observed peptide sequence of both 60 kD and 42 kD bands were identical and started with the first amino acid of the mature protein (residue #19 by Swiss-Prot), this implies that a ~18 kD fragment of the C-terminal portion of the ecto-domain was cleaved off to yield the 42 kD band and that this ~18 kD fragment presumably contains the antibody epitope and would therefore explain the loss of immunoreaction with the antibodies.

A similar strategy was implemented using two other proteases, namely trypsin and endo-GluC. Digestion of the receptor using trypsin yielded major fragments of 26, 19, and 15 kD (non-reduced), and 30 and 26 kD (reduced). All but the 15 kD fragment, which was sequenced and shown to arise from Ig-domain 1, showed immunoreactivity towards the antibodies. The 4 remaining bands (26, 19 and 26, 30 kD) showed not only immunoreactivity but also had the same peptide sequence, starting with S-N-I-V-etc. This sequence begins at residue 211 (Swiss-Prot sequence), near the predicted start of Ig-domain 3.

Using an endo-GluC digest, a dominant Coomassie stained band was observed at approximately 40 kD on a reduced gel. This band was reactive with antibodies to murine-Fc, although no reactivity was observed with anti-IL18 receptor antibodies. The N-terminal peptide sequence of this fragment, G-K-W-H-etc., begins at residue 274 (Swiss-Prot sequence) which is on the carboxy-terminal half of Ig-domain 3. This observation would imply that the epitope region does not extend C-terminal to residue 274.

The invention claimed is:

1. An isolated antibody or antibody fragment capable of specifically binding human interleukin-18 receptor alpha (hIL-18Rα), wherein the antibody comprises a light chain variable region (LCVR) comprising SEQ ID:13.

2. The antibody or antibody fragment of claim 1, characterized by binding hIL-18Rα with an $IC_{50}$ of about 7 pM, as measured by ELISA solution affinity assay.

3. The antibody or antibody fragment of claim 1, characterized by binding hIL-18Rα with a $K_D$ of about 3 pM, as determined by surface plasmon resonance.

4. The antibody or antibody fragment of claim 1, further comprising a heavy chain variable region (HCVR) comprising SEQ ID NO:11.

5. A pharmaceutical composition comprising the antibody or antibody fragment of claim 1 and a pharmaceutically acceptable carrier.

6. An isolated antibody or antibody fragment capable of specifically binding human interleukin-18 receptor alpha (hIL-18Rα), wherein the antibody comprises a HCVR comprising SEQ ID NO:11.

7. The antibody or antibody fragment of claim 6, characterized by binding hIL-18Rα with an $IC_{50}$ of about 7 pM, as measured by ELISA solution affinity assay.

8. The antibody or antibody fragment of claim 6, characterized by binding hIL-18Rα with a $K_D$ of about 3 pM, as determined by surface plasmon resonance.

9. A pharmaceutical composition comprising the antibody or antibody fragment of claim 6 and a pharmaceutically acceptable carrier.

10. An isolated antibody or antibody fragment capable of specifically binding human interleukin-18 receptor alpha (hIL-18Rα), wherein the antibody comprises a LCVR comprising the three CDRs from SEQ ID NO:13, and a HCVR comprising the three CDRs from SEQ ID NO:11.

11. The antibody or antibody fragment of claim 10, wherein light chain CDR1, CDR2 and CDR3 consist of, respectively, amino acids 27-38, 56-58 and 96-103 of SEQ ID NO:13.

12. The antibody or antibody fragment of claim 10, wherein heavy chain CDR1, CDR2 and CDR3 consist of, respectively, amino acids 26-33, 51-58 and 97-104 of SEQ ID NO:11.

13. A pharmaceutical composition comprising the antibody or antibody fragment of claim 10 and a pharmaceutically acceptable carrier.

* * * * *